(12) United States Patent
Maus et al.

(10) Patent No.: US 8,048,910 B2
(45) Date of Patent: Nov. 1, 2011

(54) COMBINATION OF R,R-GLYCOPYRROLATE, ROLIPRAM, AND BUDESONIDE FOR THE TREATMENT OF INFLAMMATORY DISEASES

(75) Inventors: Joachim Maus, Mühlheim (DE); Horst Kastrup, Münster (DE); Istvan Szelenyi, Schwaig (DE); Peter Jürgen Cnota, Bad Homburg (DE); Artur Bauhofer, Marburg (DE)

(73) Assignee: Meda Pharma GmbH & Co. KG, Bad Homburg (DE)

( * ) Notice: Subject to any disclaimer, the term of this patent is extended or adjusted under 35 U.S.C. 154(b) by 1046 days.

(21) Appl. No.: 11/642,967

(22) Filed: Dec. 21, 2006

(65) Prior Publication Data

US 2007/0196285 A1    Aug. 23, 2007

Related U.S. Application Data

(60) Provisional application No. 60/752,058, filed on Dec. 21, 2005.

(51) Int. Cl.
*A61K 31/40* (2006.01)
*A61K 31/56* (2006.01)

(52) U.S. Cl. .................. 514/428; 514/423; 514/171

(58) Field of Classification Search .............. 514/171, 514/423, 428, 651
See application file for complete search history.

(56) References Cited

U.S. PATENT DOCUMENTS

| | | | |
|---|---|---|---|
| 5,712,298 | A | 1/1998 | Amschler et al. |
| 6,086,914 | A | 7/2000 | Weinstein et al. |
| 6,204,285 | B1 | 3/2001 | Fabiano et al. |
| 6,384,038 | B1 | 5/2002 | Rubin |
| 6,475,467 | B1 | 11/2002 | Keller et al. |
| 6,645,466 | B1 | 11/2003 | Keller et al. |
| 7,258,118 | B2 | 8/2007 | Goede et al. |
| 2001/0025040 | A1 | 9/2001 | Poppe et al. |
| 2001/0027789 | A1 | 10/2001 | Goede et al. |
| 2002/0115681 | A1 | 8/2002 | Bozung et al. |
| 2002/0151597 | A1 | 10/2002 | Banerjee et al. |
| 2003/0068280 | A1 | 4/2003 | Bannister et al. |
| 2003/0119802 | A1 | 6/2003 | Gavin |
| 2004/0002548 | A1 | 1/2004 | Bozung et al. |
| 2004/0028734 | A1 | 2/2004 | Bannister et al. |
| 2004/0038958 | A1 | 2/2004 | Rundfeldt et al. |
| 2004/0053902 | A1 | 3/2004 | Smith |
| 2005/0288265 | A1* | 12/2005 | Locher et al. ............ 514/171 |
| 2006/0081246 | A1 | 4/2006 | Goede et al. |
| 2006/0147382 | A1 | 7/2006 | Bundschuh et al. |

FOREIGN PATENT DOCUMENTS

| | | |
|---|---|---|
| EP | 1449528 A1 * | 8/2004 |
| WO | WO-01/76575 | 10/2001 |
| WO | WO-02/069945 | 9/2002 |
| WO | WO-02078671 | 10/2002 |
| WO | WO-02/096423 | 12/2002 |
| WO | WO-02/096463 | 12/2002 |
| WO | WO-03/011274 | 2/2003 |
| WO | WO 2004019984 A1 * | 3/2004 |
| WO | WO-2004084897 | 10/2004 |
| WO | WO-2005005999 | 6/2005 |

OTHER PUBLICATIONS

Mueller et al. "Development of powder for inhalation with R,R-glycopyrrolate as active ingredient for the delivery from novel multidose dry powder inhaler," European Respiratory Society Annual Congress 2003, Sep. 2003, abstract 2977.*
Pahl, Andreas, Possible Synergistic Effects f R, S/S,R-glycopyrolate and Tiotropium with the Glucocorticoid Budesonide, Viatris: No. 2006-03, Jul. 19, 2006.
Austen et al. at p. 856 (Austen et al., Samter's Immunologic Diseases. Philadelphia: Lippincott Williams & Wilkins, 2001, pp. 855-856.
Brostoff et al., Clinical Immunology. London: Gower Medical Publishing, 1991, p. 17.1.
Gennaro, Alfonso. Remington's: Pharmaceutical Sciences. Easton, PA:Mack Publishing Co., 1985, p. 728.
Roitt et al. Immunology. 3rd Ed. St Louis: Mosby, 1993, p. 19.13.
Herbst et al., "Selective oral epidermal growth factor receptor tyrosine kinase inhibitor ZD1839 is generally well-tolerated and has activity in non-small-cell lung cancer and other solid tumors: results of a Phase I trial" Journal of Clinical Oncology, Sep. 15, 2002, vol. 20, No. 18. pp. 3815-3825.
Finsnes et al., "Leukotriene antagonism reduces the generation of endothelin-I and interferon-gamma and inhibits eosinophilic airway inflammation" Respiratory Medicine 2002, vol. 96, pp. 901-906.
Reid, P., "Roflumilast", Current Opinion in Investigational Drugs, Current Drugs, London, GB, vol. 3, No. 8, Aug. 2002, pp. 1165-1170.
Santing et al., "Phosphodiesterase inhibitors reduce bronchial hyperreactivity and airway inflammation in unrestrained guinea pigs", European Journal of Pharmacology, vol. 275, No. 1, pp. 75-82 (1995).
International Search Report dated Nov. 23, 2005, issued in PCT/EP2005/000649.

* cited by examiner

*Primary Examiner* — Yong Chong
*Assistant Examiner* — Jody Karol
(74) *Attorney, Agent, or Firm* — Venable LLP; Keith G. Haddaway (57) ABSTRACT

Novel combinations based on anticholinergics, $\beta_2$-adrenoceptor agonists, PDE 4 Inhibitors, glucocorticoids, and leukotriene-receptor antagonists, process for their production and their use for the treatment of inflammatory diseases, preferably respiratory diseases as bronchial asthma and chronic obstructive pulmonary diseases (COPD) or rheumatic or autoimmune diseases. A particular combination comprises R,R-glycopyrrolate, rolipram, and budesonide, or physiologically acceptable salts thereof, wherein dosage amounts are such that a synergistic therapeutic effect is achieved.

10 Claims, 2 Drawing Sheets

COMBINATION OF R,R-GLYCOPYRROLATE, ROLIPRAM, AND BUDESONIDE FOR THE TREATMENT OF INFLAMMATORY DISEASES

The invention relates to novel combinations based on anticholinergics, $\beta_2$-adrenoceptor agonists, PDE 4 Inhibitors, glucocorticoids, and leukotriene-receptor antagonists, process for their production and their use for the treatment of inflammatory diseases, preferably respiratory diseases as bronchial asthma and chronic obstructive pulmonary diseases (COPD) or rheumatic or autoimmune diseases.

Asthma bronchiale, affecting as many as 10% of individuals in industrialized nations, is characterized by bronchoconstriction, chronic airway inflammation, airway hyperreactivity, and mucosal oedema. Airway remodelling and altered noncholinergic, nonadrenergic neurotransmission may contribute to irreversible airway obstruction and reduction of pulmonary function. Asthma is characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mould, pollen, cold air, exercise, stress, tobacco smoke, and air pollutants. Bronchial asthma has emerged as a major public health problem worldwide over the past 20 years. Although data indicate that current asthma therapies led to limited decreases in death rates, it continues to be a significant health care problem. It still is one of the leading causes of preventable hospitalization worldwide and accounts for several million lost workdays. Along with the increase in asthma prevalence, the costs associated with this disease have also risen dramatically.

Chronic obstructive pulmonary disease (COPD) is very common world-wide. It is primarily associated with past and present cigarette smoking but the fact that the society gets older also plays an even continuously increasing role. The prevalence of COPD varies between 3% and 10% with a steadily increasing trend. Although COPD is a leading cause of illness and death, its recognition as a public health problem has been slow to evolve despite the rising mortality rate for COPD and the decline in death rates for most of the cardiovascular diseases (Hurd Chest 2000; 117(2 Suppl):1S-4S). Additionally, COPD imparts substantial economic burden on individuals and society. COPD is a disease characterised by chronic inflammation and irreversible airflow obstruction with a decline in the lung function parameter $FEV_1$ that is more rapid than normal. The disease has two major aspects of pathology, namely chronic bronchitis, characterised by mucus hypersecretion from the conducting airways, and emphysema, characterised by destructive changes in the alveoli.

Asthma and COPD are serious world health problems characterised by a chronic inflammatory disorder of the airways. Airflow obstruction and airway inflammation are features of asthma as well as COPD. Although the airway inflammation in asthma and COPD, respectively, involve different cell types, both diseases are of chronic inflammatory nature associated with cellular infiltration and activation. While bronchial asthma is predominantly characterized by eosinophils and CD4+ lymphocytes, neutrophil granulocytes, CD8+ lymphocytes and macrophages appear to play a major role in the pathogenesis of COPD (Saetta et al. Am J Respir Crit. Care Med 1999; 160:711-7, Shapiro Am J Respir Crit. Care Med 1999; 160:S29-S32).

There is now strong evidence that airway inflammation is a predominant underlying problem in patients with asthma and COPD.

The pathophysiology of asthma involves an interactive network of molecular and cellular interactions, although the contribution of each individual factor is probably different from patient to patient depending on the setting and stimulus. Major participants in the development of an asthma phenotype include the triggering stimuli such as the allergens themselves, cells such as T cells, epithelial cells and mast cells that produce a variety of cytokines including tumor necrosis factor-alpha (TNF$\alpha$), interleukin (IL)-5, granuloyte-macrophage colony-stimulating-factor (GM-CSF), IL-3, IL-4 and IL-13 and chemokines such as eotaxin, adhesion molecules, etc.

Unfortunately, much less is known about the pathogenesis of COPD than that of asthma. Recent studies have greatly expanded the understanding of pathogenetic mechanisms underlying COPD. Thus, there is consent that COPD is also an inflammatory disease. From the present pathogenetical point of view, COPD is defined as a progressive and not fully reversible airway obstruction with predominantly neutrophilic airway inflammation. In COPD, the predominant inflammatory cell types are $CD8^+T$ lymphocytes, macrophages, and neutrophils. Neutrophils and neutrophilic inflammatory markers including IL-8, TNF$\alpha$ and $LTB_4$ are increased in the airways of COPD patients (Yamamoto et al. Chest 1997; 112:505-10, Keatings et al. Am J Respir Crit. Care Med 1996; 153:530-4).

The current management of asthma and COPD is focussed on the improvement of the lung function of patients. In both diseases but especially in COPD, the first step is smoking cessation. There is evidence that smoking reduction or cessation may result in improvement of some respiratory parameters.

Bronchoconstriction occurs due to bronchial smooth muscle spasm and airway inflammation with oedema. $\beta_2$-adrenoceptor agonists provide a bronchodilator effect to the patients, resulting in relief from the symptoms of breathlessness. $\beta_2$-adrenoceptor agonists can be short-acting for immediate relief, or long-acting for long-term prevention of respiratory symptoms. Short-acting $\beta_2$-adrenoceptor agonists currently available include salbutamol, terbutaline, reproterol, pirbuterol, fenoterol, bitolterol. To LABAs belong compounds such as salmeterol, formoterol, indacaterol.

Whilst it is also known that $\beta_2$-adrenoceptor agonists provide symptomatic relief of patients suffering from asthma or COPD, another component of these airway disorders, i.e. inflammation often requires separate treatment. Typically this may involve treatment with a glucocorticoid, a LTRA or a PDE4 inhibitor, respectively. Currently available glucocorticoids include beclomethasone, triamcinolone, budesonide, fluticasone, mometasone, ciclesonide, loteprednol, etiprednol, flunisolide. LTRAs include pranlukast, montelukast, zafirlukast. PDE4 inhibitors are now under clinical development. Some of them are shortly before approval, e.g. roflumilast, AWD-12 281.

Bronchoconstriction and inflammation are also associated with increased bronchial mucus production and possible bronchial plugging, which can be treated with anticholinergics, such as ipratropium, oxitropium, tiotropium, glycopyrrolate and in particular the RR enantiomer of glycopyrrolate.

Bronchodilators ($\beta_2$-adrenoceptor agonists and anticholinergics) are now the mainstay of symptomatic therapy. Short- and long-acting $\beta_2$-adrenoceptor agonists such as salbutamol, fenoterol, salmeterol, formoterol are established therapeutics in the symptomatic COPD management. Of the short-acting antimuscarinic drugs, ipratropium is widely used although antimuscarinic drugs are rather less efficacious in the relief of an asthma attack than the $\beta_2$-adrenoceptor agonists (Rodrigo and Rodrigo, Chest 2003; 123:1908-15). Recently, tiotropium, a long-acting anticholinergic with a certain preference to $M_3$-muscarinic receptors has now been introduced worldwide (Hansel and Barnes, Drugs Today (Barc) 2002; 38:585-600, Koumis and Samuel, Clin Ther 2005; 27:377-92). Relatively sufficient anti-inflammatory therapy with glucocorticoids are available for asthma. However, they are less effective in COPD. Additionally, tiotropium reduces COPD exacerbations and related hospitalisations compared to placebo and ipratropium (Barr et al. Cochrane Database Syst Rev 2005; (2):CD002876). Further long-acting anticholinergics are now under development. They are more convenient to use for patients with advanced disease who require maintenance therapy with bronchodilators, and have been shown to provide superior efficacy compared with short-acting antimuscarinic agents.

The basic tenet of asthma therapy has centred on optimal management of the underlying inflammatory process. The most recent expert recommendations strongly support the use of inhaled glucocorticoids. Bronchodilators are used for transient relief of symptoms in these patients and for additional symptomatic control in patients who have persistent symptoms despite inhaled glucocorticoid therapy (http://www.ginasthma.com/). In well-defined COPD, therapeutic alternatives vary. Because there is no currently accepted pharmacologic therapy that alters the natural history of the disease, therapeutic emphasis is placed on symptom relief. Unlike in asthma therapy, bronchodilators play a prominent role in the initial therapy for symptomatic COPD patients. In this regard, long-acting $\beta_2$-adrenoceptor agonists and the new long-acting anticholinergic agent (tiotropium) offer distinct advantages. In contrast, inhaled glucocorticoids appear to have a more limited role in COPD. On the other hand, inhaled glucocorticoids have been shown to have beneficial effects on health status and to decrease exacerbation rates in COPD patients.

Autoimmune diseases (e.g. rheumatoid arthritis [RA], systemic lupus erythematosus [SLE], multiple sclerosis [MS], glomerulonephritis, inflammatory bowel diseases [Morbus Cohn, colitis ulcerosa], psoriasis) belong to the major health problems worldwide. Autoimmune diseases are among the ten leading causes of death. Most of autoimmune diseases require lifelong treatment (Jacobson D L, Gange S J, Rose N R, Graham N M. Clin Immunol Immunopathol 1997; 84:223-43).

Autoimmune diseases are disorders in which the immune system produces antibodies against the body's own cells, destroying healthy tissue. These misdirected immune responses are referred to as autoimmunity, which can be demonstrated by the presence of autoantibodies or T lymphocytes reactive with host antigens. Human autoimmune diseases can be divided into two categories: organ-specific and systemic. In organ-specific autoimmune disease (e.g. Graves' disease, Hashimoto's thyroiditis, type 1 diabetes mellitus), autoreactivity is directed to antigens unique to a single organ. In systemic autoimmune disease (e.g. RA, MS, SLE), autoreactivity is largely directed toward a broad range of antigens and involves a number of tissues.

Systemic lupus erythematosus (SLE) is a chronic, usually life-long, potentially fatal autoimmune disease. SLE is notable for unpredictable exacerbations and remissions and a predilection for clinical involvement of the joints, skin, kidney, brain, lung, heart, and gastrointestinal tract.

Rheumatoid arthritis (RA), juvenile idiopathic arthritis, the seronegative spondyloarthropathies including psoriatic arthritis, and systemic lupus erythematosus are all examples of rheumatic diseases in which inflammation is associated with skeletal pathology. RA is the most common inflammatory joint disease and a major cause of functional disability, morbidity, and premature mortality. Inflammation of the synovial membrane surrounding a joint leads to swollen, tender, and stiff joints. This may be accompanied by fatigue, weight loss, anxiety, and depression.

Rheumatoid arthritis (RA) usually requires lifelong treatment. Nonsteroidal anti-inflammatory drugs (NSAIDs) have been the cornerstone of therapy for RA. NSAIDs reduce pain and inflammation and allow for improvements in mobility and function. Aspirin and other NSAIDs, such as ibuprofen, diclofenac, fenoprofen, indomethacin, naproxen are strongly anti-flammatoric and analgetic. Their strong gastrointestinal side effects often limit their use. Cyclooxygenase-2 (COX-2) inhibitors were initially believed to cause fewer stomach problems than classical NSAIDs. However, the use of COX-2 inhibitors is considerably limited due their cardiovascular undesired effects. Corticosteroids, used alone or in conjunction with other medications, may reduce the symptomatology associated with RA. In fact, corticosteroids reduce inflammation in RA. However, because of potential long-term side effects (e.g. gastrointestinal ulceration, osteoporosis, cataract development, glaucoma, etc.), corticosteroid use is usually limited to short courses and low doses where possible. Drugs like anticholinergics are frequently used in combination with GCs to reduce ulcer development induced by GCs.

The current standard of care is aggressive therapy with anti-inflammatory drugs and disease-modifying anti-rheumatic drugs (DMARDs).

DMARDs most frequently are used in various combination therapy regimens.

Tumor necrosis factor (TNF) inhibitors are a relatively new class of medications used to treat autoimmune disease. They include etanercept (soluble TNF receptor), infliximab (monoclonal antibody against TNF), adalimumab (human TNF antibody) and anakinra (recombinant human interleukin-1 receptor antagonist).

The term inflammatory bowel disease (IBD) describes a group of chronic inflammatory disorders of unknown causes involving the gastrointestinal tract (GIT). Patients with IBD can be divided into two major groups, those with ulcerative colitis (UC) and those with Crohn's disease (CD). In patients with UC, there is an inflammatory reaction primarily involving the colonic mucosa. The inflammation is typically uniform and continuous with no intervening areas of normal mucosa. CD differs from UC in that the inflammation extends through all layers of the intestinal wall and involves mesentery as well as lymph nodes. CD can occur anywhere along the intestinal tract.

Current therapies comprise aminosalicylates, drugs that contain 5-aminosalicyclic acid (5-ASA), which help to control inflammation. Sulfasalazine is mainly useful in colonic disease because the active compound, 5-aminosalicylic acid (5-ASA), is released in the large bowel by bacterial degradation of the parent compound. Products such as mesalamine that release 5-ASA in the distal small bowel secondary to pH changes are more useful in patients with small intestinal Crohn disease. Other 5-ASA agents, such as olsalazine, mesalamine, and balsalazide, have a different carrier, fewer side effects, and may be used by people who cannot take sulfasalazine. Immunomodulators such as azathioprine and 6-mercapto-purine reduce inflammation by affecting the immune system.

Since TNF is a key inflammatory cytokine and mediator of intestinal inflammation, compounds directed against this cytokine such as infliximab are promising in IBD. In certain cases, immunosuppressive agents: cyclosporine A, tacrolimus, mycophenolate mofetil may be effective in treating IBD.

GCs such as prednisone, methylprednisone, and hydrocortisone also reduce inflammation. They can be given orally, intravenously, through an enema, or in a suppository, depending on the location of the inflammation. These drugs can cause side effects such as gastrointestinal ulceration, weight gain, acne, facial hair, hypertension, diabetes, mood swings, bone mass loss, and an increased risk of infection. For this reason, they are not recommended for long-term use, although they are considered very affective when prescribed for short-term use.

In patients who relapse after withdrawal of steroids, other treatment options are required. Steroids are not indicated for maintenance therapy because of serious complications such as aseptic necrosis of the hip, osteoporosis, cataract, diabetes, and hypertension.

Multiple sclerosis (MS) is a chronic, potentially debilitating disease that affects the central nervous system characterized by the destruction of the myelin sheath surrounding neurons, resulting in the formation of "plaques". MS is a progressive and usually fluctuating disease with exacerbations and remissions over many decades. MS affects more than 1 million people around the world.

Current therapies target the immune dysfunction in MS and resultant neural tissue damage with the goal of preventing or at least reducing the long-term risk of clinically significant disability. These therapies are currently available: interferon (IFN)-β and glatiramer acetate (Copaxone®) (Linker R A, Stadelmann C, Diem R, Bahr M, Bruck W, Gold R. Fortschr Neurol Psychiatr 2005; 73:715-27; Strueby L, Nair B, Kirk A, Taylor-Gjevre R M. J Rheumatol 2005; 34:485-8). All of these medications appear to modulate the immune response in MS, although glatiramer acetate and IFN medications probably work through different mechanisms. Each of these treatments (interferons and glatiramer acetate) offer different advantages and disadvantages. Great disadvantages are route of administration by injection and the high costs.

The key to successful treatment of MS is to slow the inflammatory process early in the disease. In order to prevent progression of disability, mitoxantrone, cyclophosphamide, methotrexate, azathioprine and cyclosporine are applied. GCs (e.g. methylprednisolone) are also frequently used. There is evidence that GCs slow down the brain atrophy progression in MS patients (Zivadinov R. J Neurol Sci 2005; 233:73-81.

Psoriasis is a chronic, recurrent autoimmune disease of variable severity that is considered to be a genetically programmed disease of dysregulated inflammation, which is driven and maintained by multiple components of the immune system.

Although topical drug preparations are usually sufficient to control psoriasis symptoms in patients with relatively mild disease, patients with moderate to severe disease usually require phototherapy or systemic drugs. The treatment of psoriasis includes ultraviolet, photochemotherapy, CsA, methotrexate and oral retinoid therapy (Naldi L, Griffiths C E. Br J Dermatol 2005; 152:597-615). There is also considerable experience supporting the efficacy of systemic therapy for psoriasis (Bissonnette R. Skin Therapy Lett 2006; 11:1-4). Many different treatment options are available to control the symptoms of psoriasis. Mild to moderate cases are often treated first with topical treatments, such as coal tar, calcipotriol, salicylic acid, GCs. However, as the disease becomes more severe, treatment options such as phototherapy, systemic medication, and new biologics are employed. Some common systemic medications include: methotrexate, cyclosporine A, retinoids, vitamin A derivatives. Biologic medications, such as T-cell modulators and TNF inhibitors (e.g. infliximab, alefacept, efalizumab etanercept), offer an alternative to other advanced therapies like systemic medications and phototherapy (Menter A, Cather J C, Baker D, Farber H F, Lebwohl M, Darif M. J Am Acad Dermatol 2006; 54:61-3; Papp K A, Miller B, Gordon K B, Caro I, Kwon P, Compton P G, Leonardi C L; J Am Acad Dermatol 2006; 54(4 Suppl 1):S164-70).

Besides the mentioned drug classes, there are several novel drugs with interesting modes of actions are now in clinical development for the treatment of autoimmune diseases.

Current therapies for autoimmune diseases are not cures, but are aimed at reducing symptoms to provide the patient with an acceptable quality of life. In organ-specific autoimmune disorders, symptoms can be corrected by metabolic control with biologically active compounds. For example, hypothroidism can be controlled by the administration of thryroxine or diabetes mellitus can be treated with injections of insulin. Drugs used in most cases of autoimmune disease, especially systemic autoimmune disease, provide general nonspecific suppression of the immune system. For the most part these drugs do not distinguish between the pathological immune response and the protective immune response. Immunosuppressive drugs (e.g., GCs, azathioprine, cyclophoshamide, CsA) are often given to suppress the proliferation of autoreactive lymphocytes. Anti-inflammatory drugs also are prescribed to patients with RA. Unfortunately these drugs, besides not working in many patients, have very serious side-effects. The general suppression of the immune response puts the patient at greater risk to infection and cancer. Additionally, NSAIDs are effective in the pain management, their use may be associated with serious systemic adverse effects, particularly gastrointestinal disorders. Therefore, current treatments for autoimmune diseases are not satisfactory. Given the high prevalence of these diseases, improved, more effective and more convenient therapeutic interventions are highly desirable. Clearly there is a significant need for agents capable of treating autoimmune diseases. It would be desirable if such therapy could be administered in a cost-effective and timely fashion, with a minimum of adverse side effects.

In general, treatment modalities in the therapy of autoimmune diseases include symptomatic treatments using anti-inflammatory drugs, immunosuppressant medications, immunomodulating therapy and others. No single regimen is appropriate. Therefore, combinations of different medications are preferred.

Various approaches have been taken to suppress this inappropriate autoimmune inflammatory response. The efficacy of different classes of drugs, e.g. GCs, PDE4 inhibitors and others have shown only limited efficacy, perhaps because blocking only one of many pathways does not provide a sufficiently large decrease in overall inflammatory processes. The other approach is the use of a combination of drugs which target several pathogenetical processes.

Glycopyrrolate belongs to the so-called anticholinergic drugs and antagonizes the neurotransmitter acetylcholine at its receptor site. This effect leads to a considerable bronchodilatation and a reduced mucus secretion. Long-acting $\beta_2$-adrenoceptor agonists (LABA) (e.g. salmeterol, formoterol, indacaterol) are the basis therapy of asthma and frequently in COPD. They stimulate the adenylate cyclase and increase the intracellular cAMP content resulting in bronchodilation. Antagonists of BLT- and CysLT-receptors reduce the inflammatory processes in the airways. Thus, these effects of LT-receptor-antagonists result in an improved mucosal and bronchial function in patients suffering from bronchial asthma or COPD. To date, one of the most effective medications for airway inflammation is inhaled glucocorticoids (GCs). These compounds practically inhibit all important inflammatory processes involved in asthma and partly in COPD, at least, to a considerable extent. Inhibitors of the isoenzyme PDE4 reduce the inflammatory processes both in asthma and COPD.

A cornerstone in the management of asthma and COPD is the control of airway inflammation. All drug classes mentioned above are able to reduce airway inflammation to various extents. Therefore, our intention was to combine these drug classes with the aim to improve the bronchodilatory effect and to enhance the anti-inflammatory activity.

The pharmacodynamic properties of all these drug classes, anticholinergics (especially R,R-glycopyrrolate), $\beta_2$-adrenoceptor agonists, antagonists of BLT- and CysLT-receptors, PDE4 inhibitors, and/or inhaled GCs complement one another and result in more efficacious treatment of the mentioned diseases, which is surprisingly over-additive even compared to the dual combinations. Furthermore, since the doses of monocompounds are in the combination lower, the incidence of adverse effects can be reduced by using the combination. Additionally, the patients' compliance is also increased.

Both short- and long-acting $\beta_2$-adrenoceptor agonists play a pivotal role in the acute and chronic management of asthma. They $\beta_2$-adrenoceptor agonists are an integral part of the treatment in COPD and asthma, and combination of two or more bronchodilator agents generally is needed to control symptoms. Patients with either condition can benefit from bronchodilators. Their major action on the airways is the relaxation of smooth muscle cells. In addition to their bronchodilator properties, $\beta_2$-adrenoceptor agonists may have other effects through their activation of $\beta_2$-adrenoceptors expressed on resident airway cells such as epithelial cells and mast cells and circulating inflammatory cells such as eosinophils and neutrophils. These non-bronchodilator activities of $\beta_2$-adrenoceptor agonists may enhance their efficacy in the management of asthma. In pre-clinical studies, the anti-inflammatory effects of $\beta_2$-adrenoceptor agonists are demonstrated through their stabilizing effect on mast cells and their inhibition of mediator release from eosinophils, macrophages T-lymphocytes, and neutrophils. In addition, $\beta_2$-adrenoceptor agonists may inhibit plasma exudation in the airway, and mediator release from epithelial cells.

The regular use of short-acting $\beta_2$-adrenoceptor agonists alone has been shown to have deleterious effects on asthma control. Therefore, short-acting agents should only be used when needed for rescue of acute symptoms. Monotherapy with long-acting $\beta_2$-adrenoceptor agonists (LABAs) has also been associated with poor asthma control. However, when given concomitantly with inhaled glucocorticoids, $\beta_2$-adrenoceptor agonists may potentiate the anti-inflammatory effect of glucocorticoid, improve asthma control and prevent exacerbations (Hanania and Moore, Curr Drug Targets Inflamm Allergy 2004; 3:271-7). Basically, the combination of LABAs and inhaled GCs is useful in both conditions.

Antimuscarinic treatment of asthma and COPD has a relatively long history leading to its present day use as an effective bronchodilating drug for obstructive pulmonary diseases. Anticholinergic agents are exemplified by the belladonna alkaloids atropine and scopolamine, which inhibit the muscarinic action of acetylcholine on structure innervated by postganglionic cholinergic nerves. These agents typically inhibit bronchoconstriction by relaxing of smooth muscles and cause considerable bronchodilation. Anticholinergic agents also are known to exert central effects which include pupil dilatation and stimulation and/or depression of the central nervous system. Novel anticholinergic pharmaceuticals have been developed which have a limited capacity to pass across the blood-brain barrier, and therefore have a limited capacity to produce central effects. Examples of these agents are the quaternary ammonium compounds methscopolamine, ipratropium, oxitropium, tiotropium and the enantiomers of glycopyrrolate. Some experts recommend ipratropium as the first choice. It has a very slow onset and can be used as maintenance therapy for people with emphysema and chronic bronchitis with few severe side effects. However, a patient should not take more than 12 inhalations per day. The recently introduced tiotropium has a long duration of action and superior to ipratropium.

Anticholinergic medications have been accepted as an important treatment modality in COPD and chronic asthma. The anticholinergic bronchodilator, the muscarinic receptor antagonist, used in this invention will be a long-acting compound. Any compound of this type can be used in this combination therapy approach. By long-lasting it is meant that the drug will have an effect on the bronchi that lasts around 12 hours or more, up to 24 hours. The recently approved long acting inhaled anticholinergic drug, tiotropium, produces sustained bronchodilation throughout the 24 hour day (Calverley et al. Thorax 2003a; 58:855-60). In fact, bronchodilators improve symptoms and quality of life, in COPD patients, but, with the exception of tiotropium, they do not significantly influence the natural course of the disease (Caramori and Adcock, Pulm Pharmacol Ther 2003; 16:247-77).

Glycopyrrolate, a quaternary ammonium anticholinergic compound, consists of four stereoisomers. It is poorly absorbed from mucus membranes, thus reducing anticholinergic side effects (Ali-Melkkila et al. Acta Anaesthesiol Scand 1993; 37:633-42). Glycopyrrolate possesses no selectivity in its binding to the $M_1$-$M_3$ receptors. Kinetics studies, however, showed that glycopyrrolate dissociates slowly from $M_3$ muscarinic receptors (Haddad et al. Br J Pharmacol 1999; 127:413-20). Similarly to tiotropium, this behavior explains glycopyrrolate's relative receptor selectivity and its long duration of action. Indeed, there is evidence that racemic glycopyrrolate produces considerable and long-lasting bronchodilatory effects both in asthmatic and in COPD patients (Walker et al. Chest 1987; 91:49-51, Schroeckenstein et al. J Allergy Clin Immunol 1988; 82:115-9, Gilman et al. Chest 1990; 98:1095-8, Cydulka and Emerman, Ann Emerg Med 1995; 25:470-3, Hansel et al. Chest 2005; 128:1974-9). As asthma and COPD are characterized by increased mucus secretions, the antisecretory effect of anticholinergics such glycopyrrolate is an additional advantage for their use in the therapy of these diseases.

A cornerstone in the management of asthma and COPD is the control of airway inflammation.

Inhaled glucocorticoids (GCs) are the most effective long-term therapy in controlling chronic asthma symptoms (Barnes Ernst Schering Res Found Workshop. 2002; 40:1-23). Randomized, controlled clinical studies confirm the efficacy of early intervention with inhaled glucocorticoids in patients with mild persistent asthma (Sheffer et al. Ann Allergy Asthma Immunol 2005; 94:48-54). Inhaled glucocorticoids suppress eosinophilic inflammation in the airways and are a corner-stone in asthma treatment (van Rensen et al. Thorax 1999; 54:403-8, Barnes Ernst Schering Res Found Workshop. 2002; 40:1-23). However, patients show a variable response to inhaled glucocorticoids and some exhibit glucocorticoid resistance.

In COPD the airway inflammation is quite different from asthma, so inflammation and anti-inflammatory treatment in COPD is relatively a new focus of interest. In contrast to asthma, the practice of using inhaled glucocorticoids in COPD is common but controversial (Crapo et al. Eur Respir J Suppl 2003; 41:19s-28s, O'Riordan, J Aerosol Med 2003; 16:1-8). It is likely that inhaled GCs have little effect on the progression of COPD (Vonk et al. Thorax 2003; 58, 322-327). glucocorticoids are probably scarcely effective in COPD patients without overlapping concomitant asthma. The use of inhaled glucocorticoids in patients with moderately severe disease ($FEV_1$<50% predicted) may produce clinical benefit as measured by an increase in $FEV_1$, reduced symptoms and fewer exacerbations (O'Riordan, J Aerosol Med 2003; 16:1-8). However, there is also clinical evidence that the neutrophil inflammation may be decreased by inhaled glucocorticoids in clinically stable COPD patients (Yildiz et al. Respiration 2000; 67:71-6). Consequently, in a recently published guideline on COPD treatment, adding on inhaled glucocorticoid is recommended in moderate to severe disease (Pauwels et al. Am J Respir Crit. Care Med 2001; 163:1256-76). glucocorticoids should mainly be used to reduce exacerbations and improve the health status of these patients (Nishimura et al. Chest 1999; 115:31-7, Selroos, Curr Med Res Opin 2004; 20:1579-93). But it has to be admitted that current pharmacological treatment of COPD is unsatisfactory, as it does not significantly influence the severity of the disease or its natural course. In general, inhaled glucocorticoids have relatively little impact on the inflammatory processes that characterize COPD (Adcock and Chung, Curr Opin Investig Drugs 2002; 3:58-60) and are not suitable for monotherapy in COPD but can be helpfully combined with an inhaled bronchodilator (Calverley et al. Eur Respir J 2003b; 22:912 9, Calverley Semin Respir Crit. Care Med 2005; 26:235-45). They have, however, been shown to decrease the frequency of exacerbations and improve quality of life in patients with COPD (Calverley Semin Respir Crit. Care Med 2005; 26:235-45).

The administration of inhaled glucocorticoids or anticholinergics (e.g. ipratropium) reduced the risk of hospitalization of COPD patients (Rascati et al. Clin Ther 2005; 27:346-54). The combination of long-acting muscarinic antagonists and inhaled glucocorticoids is more efficacious in asthma and COPD than either alone. Indeed, there is evidence that corticosteroid/muscarinic antagonist combination therapy has complementary, additive, or synergistic inhibitory effects on proinflammatory signalling pathways, inflammatory mediator release, and recruitment and survival of inflammatory cells. In the patient with an airway inflammatory disease such as asthma or COPD, this is reflected in enhanced anti-inflammatory activity with combination therapy beyond that which can be achieved by either drug alone, or the potential for antimuscarinic drugs to provide a steroid-sparing effect.

Leukotriene receptor antagonists (LTRA) are a relatively new anti-inflammatory class of anti-asthma drugs. Leukotrienes (LTs) and their receptors play an important role in the pathogenesis of asthma, and they are also involved in COPD. More recently, the potential involvement of the monocyte-macrophage lineage in the etiology of COPD has received growing attention as a target for leukotriene inhibition (Kilfeather Chest 2002; 121(5 Suppl):197S-200S). The main effects mediated via LTs are bronchoconstriction, airway inflammation, edema and mucus hypersecretion. Arachidonic acid metabolism via 5-lipoxygenase (5-LOX) results in a group of biologically active lipids known as LTs. $LTB_4$ is a potent activator of leukocyte chemotaxis. Cysteinyl-LTs ($LTC_4$, $LTD_4$, $LTE_4$) account for the spasmogenic activity previously described as slow-reacting substance of anaphylaxis (SRS-A). These inflammatory mediators are produced by a number of cell types including mast cells, neutrophils, eosinophils, basophils, macrophages and monocytes. They exert their biological effects by binding and activating specific receptors ($LTB_4$ at the BLT receptor, cysteinyl-LTs at the $cysLT_1$-receptor). This occurs in a series of events that lead to contraction of the human airway smooth muscle, chemotaxis and increased vascular permeability, mucus hypersecretion, decrease of ciliary motility. These effects have led to their important role in the diseases of asthma, allergic rhinitis and COPD. CysLT-receptor antagonists (zafirlukast, montelukast and pranlukast) represent an effective and well-tolerated treatment for asthma in adults and children, particularly for exercise- and aspirin-induced asthma. According to current guidelines for asthma management, anti-inflammatory therapy with inhaled glucocorticoids is the cornerstone in the treatment of persistent asthma. To further optimize asthma control, add-on therapy with LABA or LTRA should be combined with low to high doses of inhaled glucocorticoids. While the first combination focuses on optimal control of symptoms and lung function, the second provides a more complete suppression of the airway inflammation. They can also have clinical applications in the COPD. Recently, it has been suggested that zafirlukast, a cysLT-receptor antagonist may increase the tidal volume and alveolar ventilation in patients suffering from COPD (Bu et al. Chin Med J 2003; 116:459-461).

Even if there are no compelling clinical data for an additional contribution by $LTB_4$ in human asthma, in other respiratory conditions such as COPD, which are characterised by pronounced neutrophil infiltration, it may be that the chemotactic properties of $LTB_4$ are more important (Daniel and O'Byrne, Am Rev Respir Dis 1991; 143:S3-5). In patients suffering from COPD, the enhanced oxidative stress is paralleled by the increased ability of neutrophil to synthesize the chemotactic factor $LTB_4$, and may ultimately contribute to the infiltration/activation of neutrophils into the airways of COPD patients (Santus et al. Am J Respir Crit. Care Med 2005; 171:838-43). Additionally, there is a selective increase in exhaled $LTB_4$ in patients with COPD (Montuschi et al. Thorax 2003; 58:585-8).

Cyclic adenosine monophosphate (adenosine 3',5'-cyclic monophosphate, [cAMP]) is known as a second messenger that mediates cellular responses to several compounds e.g. hormones, mediators, etc. Phosphodiesterases (PDEs) are a family of enzymes that metabolize 3',5' cyclic nucleotides to 5' nucleoside monophosphates, thereby terminating cAMP and cGMP second messenger activity. A particular PDE, PDE4, which is a high affinity, cAMP specific, type 4 PDE, has generated interest as potential targets for the development of novel anti-inflammatory compounds. In fact, PDE4 regulate intracellular levels of cAMP and are the predominant PDE expressed in inflammatory cells. Inhibitors of PDE4 act by increasing intracellular concentrations of cyclic AMP, which has a broad range of anti-inflammatory effects on various key effector cells involved in asthma and COPD (Barnette et al. J Pharmacol Exp Ther 1998; 284:420-6, Hatzelmann and Schudt, J Pharmacol Exp Ther 2001; 297:267-79, Marx et al. Pulm Pharmacol Ther 2002; 15:7-15, Kuss et al. J Pharmacol Exp Ther 2003; 307:373-85). They show a broad spectrum of activity in animal models of asthma COPD (Howell et al. 1995, Bundschuh et al. 2002, Billah et al. 2002, Kuss et al. J Pharmacol Exp Ther 2003; 307:373-85). In addition, activation of the cAMP signalling pathway in airway smooth muscle cells promotes relaxation and blocks smooth muscle cell replication (Tomlinson et al. Biochem Pharmacol 1995; 49: 1809-19), thus preventing the airway remodelling observed in the chronic stage of the diseases. Studies on cilomilast, roflumilast and other PDE4 inhibitors in asthma and COPD have shown a broad range of anti-inflammatory activity, and the available evidence on clinical outcomes (Compton et al. Lancet 2001; 358:265-7, Dyke and Montana, Expert Opin Investig Drugs 2002; 11:1-13, Grootendorst et al. Pulm Pharmacol Ther 2003; 16:341-7, Spina Curr Drug Targets Inflamm Allergy 2004; 3:231-6, Lipworth Lancet 2005; 365:167-75, Baumer et al. Exp Rev 2005; 1:134-45, Rabe et al. Lancet 2005; 366:563-71). Efforts to minimize or eliminate the above-mentioned adverse events sometimes associated with PDE4 inhibitors have included creating inhibitors which do not penetrate the central nervous system, and administering PDE4 inhibitors by inhalation rather than orally. It is likely that these class-associated side effects, mainly nausea and emesis, could be at least partially overcome by the so-called "second-generation" PDE4 inhibitors that can be applied by inhalation.

The PDE4 inhibitor useful in this invention may be any compound that is known to inhibit the PDE4 enzyme and which is discovered to act as highly specific PDE4 inhibitors and which is preferably used per inhalationem. For example, preclinical and clinical studies with the highly potent and selective PDE4 inhibitor AWD 12-281 showed that this compound has a good preclinical and clinical efficacy. In Brown Norway rats, AWD 12-281 suppressed allergen-induced airway eosinophilia with an $ID_{50}$ of 7 µg/kg when administered directly into the lungs. The $ID_{50}$-value of the known glucocorticoid beclomethasone was comparable (0.1 µg/kg). Due to its unique metabolic profile, the compound has a suitable safety profile after topical (nasal or inhaled) administration. When AWD 12-281 given to dogs by inhalation, no emesis could be induced up to the highest feasible dose (15 mg/kg) indicating that AWD 12-281 is useful for the inhaled treatment of asthma and COPD (Kuss et al. J Pharmacol Exp Ther 2003; 307:373-85).

Inhibition of PDE4 results in an elevation of cAMP in the inflammatory cells, which in turn downregulates the inflammatory response. For example, rolipram, a PDE4 inhibitor, reduced the clinical and histological severity of collagen-induced arthritis in rats (Nyman U, Mussener A, Larsson E, Lorentzen J, Klareskog L: Amelioration of collagen II-induced arthritis in rats by the type IV phosphodiesterase inhibitor rolipram.). It has also been demonstrated that selective PDE4 inhibition suppresses the clinical manifestations of EAE (Sommer N, Martin R, McFarland H F, Quigley L, Cannella B, Raine C S, Scott D E, Loschmann P A, Racke M K. Therapeutic potential of phosphodiesterase type 4 inhibition in chronic autoimmune demyelinating disease. J Neuroimmunol 1997; 79:54-61). PDE4 inhibitors might also have therapeutic benefit both in IBD (Banner K H, Trevethick M A. PDE4 inhibition: a novel approach for the treatment of inflammatory bowel disease. Trends Pharmacol Sci 2004; 25:430-6), and in psoriasis (Houslay M D, Schafer P, Zhang K Y. Keynote review: phosphodiesterase-4 as a therapeutic target. Drug Discov Today 2005; 10:1503-19).

One of the possible side effects induced by PDE4 inhibitors may be a certain sedation, decrease in locomotor activity. In animal experiments, it has convincingly been demonstrated that rolipram, a specific PDE4 inhibitor induces sedative effects such as hypoactivity, decreased locomotion that were completely reversed by adding scopolamine, an anticholinergic compound (Silvestre et al. Pharmacol Biochem Behav 1999; 64:1-5). Consequently, an antimuscarinic agents may compensate the possible sedation induced by a PDE4 inhibitor and thus improve the therapeutic value of the combination.

It is well known that inhaled glucocorticoids represent a first choice pharmacological intervention in the therapy of inflammatory respiratory diseases. This class of drugs, among which can be mentioned for example triamcinolone, beclomethasone, mometasone, fluticasone, budesonide, etc., elicits remarkable pharmacodynamics effects on the respiratory tract. Additionally, they also elicit undesired effects on different organs, and for this reason both their clinical use and its interruption cause a series of side effects, some of which very serious.

Among said toxic effects can be mentioned those affecting the bone tissue leading to an altered cellular metabolism and a high osteoporosis incidence. Several studies showed that inhaled glucocorticoids cause a reduction in bone mineral density leading to an increase in fractures in people taking an inhaled glucocorticoid compared with controls (Ip et al. Chest 1994; 1051722-7, Mortimer et al. Ann Allergy Asthma Immunol 2005; 94:15-21). Strategies are needed to reduce the systemic effects of inhaled glucocorticoids. Inhibition of PDE4 activity is believed effective for the treatment of osteoporosis by reducing bone loss. There is evidence that the PDE4 isoenzyme may play an important role in bone turnover through cAMP and that its inhibitors are candidates for therapeutic drugs for the bone loss diseases (Miyamoto et al. Biochem Pharmacol 1997; 54:613-7). Indeed, rolipram can enhance physiological bone formation and thereby increase bone mass in mice (Kinoshita et al. Bone 2000; 27:811-7). PDE4 inhibitors are apparently able to counteract the bone-demineralising effect of glucocorticoids. Therefore, it would be desirable to provide novel compositions that contain besides glucocorticoids PDE4 inhibitors as well.

There is evidence that inhaled glucocorticoids are especially advantageous in combination with bronchodilators (Donohue et al. Treat Respir Med 2004; 3:173-81). Furthermore, it has also been demonstrated that $\beta_2$-adrenoceptor agonists added to the existing therapy regimen consisting of an anticholinergic (ipratropium) and an inhaled glucocorticoid (beclomethasone) provides greater symptomatic relief and improvement in lung function than placebo (Gupta and Chhabra, Indian J Chest Dis Allied Sci 2002; 44:165-72).

Current treatments for asthma and COPD are not satisfactory. Given the high prevalence of these diseases, improved, more effective and more convenient therapeutic interventions are highly desirable.

Therefore the problem underlying the invention was to present a pharmaceutical, which is improved for the treatment of inflammatory diseases especially respiratory diseases as asthma or COPD, but also for rheumatism or auto-immune diseases.

This problem is solved by a combination of at least three different pharmaceutically active substances or their physiologically acceptable salts selected from the group of anticholinergics, PDE4 inhibitors, glucocorticoids, $\beta_2$-adrenoceptor agonists and Leukotriene-receptor antagonists, which show higher efficiency and reduced side effects compared to the single substances or double combinations which could not be expected from prior art.

The combinations comprise at least three different pharmaceutically active substances or their pharmaceutically acceptable salts selected from of the following groups:

A: anticholinergics: 1: methscopolamine, 2: ipratropium, 3: oxitropium, 4: tiotropium 5: racemic glycopyrrolate, 6: R,R-glycopyrrolate B: PDE 4 Inhibitors 1: rolipram, 2: roflumilast, 3: cilomilast, 4:AWD-12-281

C: Glucocorticoids: 1: budesonide, 2: fluticasone, 3: mometasone, 4: beclomethasone, 5: ciclesonide, 6: triamcinolone, 7: loteprednol, 8: etiprednol, 9: flunisolide D: $\beta_2$-adrenoceptor agonists 1: salbutamol, 2: terbutaline, 3: salmeterol, 4: formoterol, 5: indacaterol 6: fenoterol, 7: reproterol, 8: pirbuterol, 9: bitolterol E: Leukotriene-receptor antagonists 1: pranlukast, 2: montelukast, 3: zafirlukast Preferred combinations comprise three different pharmaceutically active substances or their pharmaceutically acceptable salts selected from the groups of Anticholinergics, PDE4 inhibitors and Glucocorticoids Anticholinergics, PDE4 inhibitors and $\beta_2$-adrenoceptor agonists Anticholinergics, PDE4 inhibitors and Leukotriene-receptor antagonists Anticholinergics, Glucocorticoids, and $\beta_2$-adrenoceptor agonists Anticholinergics, Glucocorticoids, and Leukotriene-receptor antagonists PDE4 inhibitors, Glucocorticoids, and $\beta_2$-adrenoceptor agonists PDE4 inhibitors, $\beta_2$-adrenoceptor agonists, and Leukotriene-receptor antagonists Glucocorticoids, $\beta_2$-adrenoceptor agonists, and Leukotriene-receptor antagonists Especially preferred combinations are comprising three different pharmaceutically active substances or their pharmaceutically acceptable salts selected from the groups of R,R-glycopyrrolate, PDE4 inhibitors and Glucocorticoids R,R-glycopyrrolate, PDE4 inhibitors and $\beta_2$-adrenoceptor agonists R,R-glycopyrrolate, PDE4 inhibitors and Leukotriene-receptor antagonists R,R-glycopyrrolate, Glucocorticoids, and $\beta_2$-adrenoceptor agonists R,R-glycopyrrolate, Glucocorticoids, and Leukotriene-receptor antagonists The following combinations show the effects according to the invention:

A1, B1, C1; A1, B1, C2; A1, B1, C3; A1, B1, C4; A1, B1, C5; A1, B1, C6; A1, B1, C7; A1, B1, C8; A1, B1, C9;
A1, B2, C1; A1, B2, C2; A1, B2, C3; A1, B2, C4; A1, B2, C5; A1, B2, C6; A1, B2, C7; A1, B2, C8; A1, B2, C9;
A1, B3, C1; A1, B3, C2; A1, B3, C3; A1, B3, C4; A1, B3, C5; A1, B3, C6; A1, B3, C7; A1, B3, C8; A1, B3, C9;
A1, B4, C1; A1, B4, C2; A1, B4, C3; A1, B4, C4; A1, B4, C5; A1, B4, C6; A1, B4, C7; A1, B4, C8; A1, B4, C9;
A2, B1, C1; A2, B1, C2; A2, B1, C3; A2, B1, C4; A2, B1, C5; A2, B1, C6; A2, B1, C7; A2, B1, C8; A2, B1, C9;
A2, B2, C1; A2, B2, C2; A2, B2, C3; A2, B2, C4; A2, B2, C5; A2, B2, C6; A2, B2, C7; A2, B2, C8; A2, B2, C9;
A2, B3, C1; A2, B3, C2; A2, B3, C3; A2, B3, C4; A2, B3, C5; A2, B3, C6; A2, B3, C7; A2, B3, C8; A2, B3, C9;
A2, B4, C1; A2, B4, C2; A2, B4, C3; A2, B4, C4; A2, B4, C5; A2, B4, C6; A2, B4, C7; A2, B4, C8; A2, B4, C9;
A3, B1, C1; A3, B1, C2; A3, B1, C3; A3, B1, C4; A3, B1, C5; A3, B1, C6; A3, B1, C7; A3, B1, C8; A3, B1, C9;
A3, B2, C1; A3, B2, C2; A3, B2, C3; A3, B2, C4; A3, B2, C5; A3, B2, C6; A3, B2, C7; A3, B2, C8; A3, B2, C9;
A3, B3, C1; A3, B3, C2; A3, B3, C3; A3, B3, C4; A3, B3, C5; A3, B3, C6; A3, B3, C7; A3, B3, C8; A3, B3, C9;
A3, B4, C1; A3, B4, C2; A3, B4, C3; A3, B4, C4; A3, B4, C5; A3, B4, C6; A3, B4, C7; A3, B4, C8; A3, B4, C9;
A4, B1, C1; A4, B1, C2; A4, B1, C3; A4, B1, C4; A4, B1, C5; A4, B1, C6; A4, B1, C7; A4, B1, C8; A4, B1, C9;
A4, B2, C1; A4, B2, C2; A4, B2, C3; A4, B2, C4; A4, B2, C5; A4, B2, C6; A4, B2, C7; A4, B2, C8; A4, B2, C9;
A4, B3, C1; A4, B3, C2; A4, B3, C3; A4, B3, C4; A4, B3, C5; A4, B3, C6; A4, B3, C7; A4, B3, C8; A4, B3, C9;
A4, B4, C1; A4, B4, C2; A4, B4, C3; A4, B4, C4; A4, B4, C5; A4, B4, C6; A4, B4, C7; A4, B4, C8; A4, B4, C9;
A5, B1, C1; A5, B1, C2; A5, B1, C3; A5, B1, C4; A5, B1, C5; A5, B1, C6; A5, B1, C7; A5, B1, C8; A5, B1, C9;
A5, B2, C1; A5, B2, C2; A5, B2, C3; A5, B2, C4; A5, B2, C5; A5, B2, C6; A5, B2, C7; A5, B2, C8; A5, B2, C9;
A5, B3, C1; A5, B3, C2; A5, B3, C3; A5, B3, C4; A5, B3, C5; A5, B3, C6; A5, B3, C7; A5, B3, C8; A5, B3, C9;
A5, B4, C1; A5, B4, C2; A5, B4, C3; A5, B4, C4; A5, B4, C5; A5, B4, C6; A5, B4, C7; A5, B4, C8; A5, B4, C9;
A6, B1, C1; A6, B1, C2; A6, B1, C3; A6, B1, C4; A6, B1, C5; A6, B1, C6; A6, B1, C7; A6, B1, C8; A6, B1, C9;
A6, B2, C1; A6, B2, C2; A6, B2, C3; A6, B2, C4; A6, B2, C5; A6, B2, C6; A6, B2, C7; A6, B2, C8; A6, B2, C9;
A6, B3, C1; A6, B3, C2; A6, B3, C3; A6, B3, C4; A6, B3, C5; A6, B3, C6; A6, B3, C7; A6, B3, C8; A6, B3, C9;
A6, B4, C1; A6, B4, C2; A6, B4, C3; A6, B4, C4; A6, B4, C5; A6, B4, C6; A6, B4, C7; A6, B4, C8; A6, B4, C9;
A1, B1, D1; A1, B1, D2; A1, B1, D3; A1, B1, D4; A1, B1, D5; A1, B1, D6; A1, B1, D7; A1, B1, D8; A1, B1, D9;
A1, B2, D1; A1, B2, D2; A1, B2, D3; A1, B2, D4; A1, B2, D5; A1, B2, D6; A1, B2, D7; A1, B2, D8; A1, B2, D9;
A1, B3, D1; A1, B3, D2; A1, B3, D3; A1, B3, D4; A1, B3, D5; A1, B3, D6; A1, B3, D7; A1, B3, D8; A1, B3, D9;
A1, B4, D1; A1, B4, D2; A1, B4, D3; A1, B4, D4; A1, B4, D5; A1, B4, D6; A1, B4, D7; A1, B4, D8; A1, B4, D9;
A3, B1, D1; A3, B1, D2; A3, B1, D3; A3, B1, D4; A3, B1, D5; A3, B1, D6; A3, B1, D7; A3, B1, D8; A3, B1, D9;
A3, B2, D1; A3, B2, D2; A3, B2, D3; A3, B2, D4; A3, B2, D5; A3, B2, D6; A3, B2, D7; A3, B2, D8; A3, B2, D9;
A3, B3, D1; A3, B3, D2; A3, B3, D3; A3, B3, D4; A3, B3, D5; A3, B3, D6; A3, B3, D7; A3, B3, D8; A3, B3, D9;
A3, B4, D1; A3, B4, D2; A3, B4, D3; A3, B4, D4; A3, B4, D5; A3, B4, D6; A3, B4, D7; A3, B4, D8; A3, B4, D9;
A4, B1, D1; A4, B1, D2; A4, B1, D3; A4, B1, D4; A4, B1, D5; A4, B1, D6; A4, B1, D7; A4, B1, D8; A4, B1, D9;
A4, B2, D1; A4, B2, D2; A4, B2, D3; A4, B2, D4; A4, B2, D5; A4, B2, D6; A4, B2, D7; A4, B2, D8; A4, B2, D9;
A4, B3, D1; A4, B3, D2; A4, B3, D3; A4, B3, D4; A4, B3, D5; A4, B3, D6; A4, B3, D7; A4, B3, D8; A4, B3, D9;
A4, B4, D1; A4, B4, D2; A4, B4, D3; A4, B4, D4; A4, B4, D5; A4, B4, D6; A4, B4, D7; A4, B4, D8; A4, B4, D9;
A5, B1, D1; A5, B1, D2; A5, B1, D3; A5, B1, D4; A5, B1, D5; A5, B1, D6; A5, B1, D7; A5, B1, D8; A5, B1, D9;
A5, B2, D1; A5, B2, D2; A5, B2, D3; A5, B2, D4; A5, B2, D5; A5, B2, D6; A5, B2, D7; A5, B2, D8; A5, B2, D9;
A5, B3, D1; A5, B3, D2; A5, B3, D3; A5, B3, D4; A5, B3, D5; A5, B3, D6; A5, B3, D7; A5, B3, D8; A5, B3, D9;
A5, B4, D1; A5, B4, D2; A5, B4, D3; A5, B4, D4; A5, B4, D5; A5, B4, D6; A5, B4, D7; A5, B4, D8; A5, B4, D9;
A6, B1, D1; A6, B1, D2; A6, B1, D3; A6, B1, D4; A6, B1, D5; A6, B1, D6; A6, B1, D7; A6, B1, D8; A6, B1, D9;
A6, B2, D1; A6, B2, D2; A6, B2, D3; A6, B2, D4; A6, B2, D5; A6, B2, D6; A6, B2, D7; A6, B2, D8; A6, B2, D9;
A6, B3, D1; A6, B3, D2; A6, B3, D3; A6, B3, D4; A6, B3, D5; A6, B3, D6; A6, B3, D7; A6, B3, D8; A6, B3, D9;
A6, B4, D1; A6, B4, D2; A6, B4, D3; A6, B4, D4; A6, B4, D5; A6, B4, D6; A6, B4, D7; A6, B4, D8; A6, B4, D9;
A1, B1, E1; A1, B1, E2; A1, B1, E3; A1, B1, E4; A1, B2, E1; A1, B2, E2; A1, B2, E3; A1, B2, E4;
A1, B3, E1; A1, B3, E2; A1, B3, E3; A1, B3, E4;

A1, B4, E1; A1, B4, E2; A1, B4, E3; A1, B4, E4;
A2, B1, E1; A2, B1, E2; A2, B1, E3; A2, B1, E4;
A2, B2, E1; A2, B2, E2; A2, B2, E3; A2, B2, E4;
A2, B3, E1; A2, B3, E2; A2, B3, E3; A2, B3, E4;
A2, B4, E1; A2, B4, E2; A2, B4, E3; A2, B4, E4;
A3, B1, E1; A3, B1, E2; A3, B1, E3; A3, B1, E4;
A3, B2, E1; A3, B2, E2; A3, B2, E3; A3, B2, E4;
A3, B3, E1; A3, B3, E2; A3, B3, E3; A3, B3, E4;
A3, B4, E1; A3, B4, E2; A3, B4, E3; A3, B4, E4;
A4, B1, E1; A4, B1, E2; A4, B1, E3; A4, B1, E4;
A4, B2, E1; A4, B2, E2; A4, B2, E3; A4, B2, E4;
A4, B3, E1; A4, B3, E2; A4, B3, E3; A4, B3, E4;
A4, B4, E1; A4, B4, E2; A4, B4, E3; A4, B4, E4;
A5, B1, E1; A5, B1, E2; A5, B1, E3; A5, B1, E4;
A5, B2, E1; A5, B2, E2; A5, B2, E3; A5, B2, E4;
A5, B3, E1; A5, B3, E2; A5, B3, E3; A5, B3, E4;
A5, B4, E1; A5, B4, E2; A5, B4, E3; A5, B4, E4;
A6, B1, E1; A6, B1, E2; A6, B1, E3; A6, B1, E4;
A6, B2, E1; A6, B2, E2; A6, B2, E3; A6, B2, E4;
A6, B3, E1; A6, B3, E2; A6, B3, E3; A6, B3, E4;
A6, B4, E1; A6, B4, E2; A6, B4, E3; A6, B4, E4;
A1, C1, D1; A1, C1, D2; A1, C1, D3; A1, C1, D4; A1, C1, D5; A1, C1, D6; A1, C1, D7; A1, C1, D8; A1, C1, D9;
A1, C2, D1; A1, C2, D2; A1, C2, D3; A1, C2, D4; A1, C2, D5; A1, C2, D6; A1, C2, D7; A1, C2, D8; A1, C2, D9;
A1, C3, D1; A1, C3, D2; A1, C3, D3; A1, C3, D4; A1, C3, D5; A1, C3, D6; A1, C3, D7; A1, C3, D8; A1, C3, D9;
A1, C4, D1; A1, C4, D2; A1, C4, D3; A1, C4, D4; A1, C4, D5; A1, C4, D6; A1, C4, D7; A1, C4, D8; A1, C4, D9;
A1, C5, D1; A1, C5, D2; A1, C5, D3; A1, C5, D4; A1, C5, D5; A1, C5, D6; A1, C5, D7; A1, C5, D8; A1, C5, D9;
A1, C6, D1; A1, C6, D2; A1, C6, D3; A1, C6, D4; A1, C6, D5; A1, C6, D6; A1, C6, D7; A1, C6, D8; A1, C6, D9;
A1, C7, D1; A1, C7, D2; A1, C7, D3; A1, C7, D4; A1, C7, D5; A1, C7, D6; A1, C7, D7; A1, C7, D8; A1, C7, D9;
A1, C8, D1; A1, C8, D2; A1, C8, D3; A1, C8, D4; A1, C8, D5; A1, C8, D6; A1, C8, D7; A1, C8, D8; A1, C8, D9;
A1, C9, D1; A1, C9, D2; A1, C9, D3; A1, C9, D4; A1, C9, D5; A1, C9, D6; A1, C9, D7; A1, C9, D8; A1, C9, D9;
A2, C1, D1; A2, C1, D2; A2, C1, D3; A2, C1, D4; A2, C1, D5; A2, C1, D6; A2, C1, D7; A2, C1, D8; A2, C1, D9;
A2, C2, D1; A2, C2, D2; A2, C2, D3; A2, C2, D4; A2, C2, D5; A2, C2, D6; A2, C2, D7; A2, C2, D8; A2, C2, D9;
A2, C3, D1; A2, C3, D2; A2, C3, D3; A2, C3, D4; A2, C3, D5; A2, C3, D6; A2, C3, D7; A2, C3, D8; A2, C3, D9;
A2, C4, D1; A2, C4, D2; A2, C4, D3; A2, C4, D4; A2, C4, D5; A2, C4, D6; A2, C4, D7; A2, C4, D8; A2, C4, D9;
A2, C5, D1; A2, C5, D2; A2, C5, D3; A2, C5, D4; A2, C5, D5; A2, C5, D6; A2, C5, D7; A2, C5, D8; A2, C5, D9;
A2, C6, D1; A2, C6, D2; A2, C6, D3; A2, C6, D4; A2, C6, D5; A2, C6, D6; A2, C6, D7; A2, C6, D8; A2, C6, D9;
A2, C7, D1; A2, C7, D2; A2, C7, D3; A2, C7, D4; A2, C7, D5; A2, C7, D6; A2, C7, D7; A2, C7, D8; A2, C7, D9;
A2, C8, D1; A2, C8, D2; A2, C8, D3; A2, C8, D4; A2, C8, D5; A2, C8, D6; A2, C8, D7; A2, C8, D8; A2, C8, D9;
A2, C9, D1; A2, C9, D2; A2, C9, D3; A2, C9, D4; A2, C9, D5; A2, C9, D6; A2, C9, D7; A2, C9, D8; A2, C9, D9;
A3, C1, D1; A3, C1, D2; A3, C1, D3; A3, C1, D4; A3, C1, D5; A3, C1, D6; A3, C1, D7; A3, C1, D8; A3, C1, D9;
A3, C2, D1; A3, C2, D2; A3, C2, D3; A3, C2, D4; A3, C2, D5; A3, C2, D6; A3, C2, D7; A3, C2, D8; A3, C2, D9;
A3, C3, D1; A3, C3, D2; A3, C3, D3; A3, C3, D4; A3, C3, D5; A3, C3, D6; A3, C3, D7; A3, C3, D8; A3, C3, D9;
A3, C4, D1; A3, C4, D2; A3, C4, D3; A3, C4, D4; A3, C4, D5; A3, C4, D6; A3, C4, D7; A3, C4, D8; A3, C4, D9;
A3, C5, D1; A3, C5, D2; A3, C5, D3; A3, C5, D4; A3, C5, D5; A3, C5, D6; A3, C5, D7; A3, C5, D8; A3, C5, D9;
A3, C6, D1; A3, C6, D2; A3, C6, D3; A3, C6, D4; A3, C6, D5; A3, C6, D6; A3, C6, D7; A3, C6, D8; A3, C6, D9;
A3, C7, D1; A3, C7, D2; A3, C7, D3; A3, C7, D4; A3, C7, D5; A3, C7, D6; A3, C7, D7; A3, C7, D8; A3, C7, D9;
A3, C8, D1; A3, C8, D2; A3, C8, D3; A3, C8, D4; A3, C8, D5; A3, C8, D6; A3, C8, D7; A3, C8, D8; A3, C8, D9;
A3, C9, D1; A3, C9, D2; A3, C9, D3; A3, C9, D4; A3, C9, D5; A3, C9, D6; A3, C9, D7; A3, C9, D8; A3, C9, D9;
A4, C1, D1; A4, C1, D2; A4, C1, D3; A4, C1, D4; A4, C1, D5; A4, C1, D6; A4, C1, D7; A4, C1, D8; A4, C1, D9;
A4, C2, D1; A4, C2, D2; A4, C2, D3; A4, C2, D4; A4, C2, D5; A4, C2, D6; A4, C2, D7; A4, C2, D8; A4, C2, D9;
A4, C3, D1; A4, C3, D2; A4, C3, D3; A4, C3, D4; A4, C3, D5; A4, C3, D6; A4, C3, D7; A4, C3, D8; A4, C3, D9;
A4, C4, D1; A4, C4, D2; A4, C4, D3; A4, C4, D4; A4, C4, D5; A4, C4, D6; A4, C4, D7; A4, C4, D8; A4, C4, D9;
A4, C5, D1; A4, C5, D2; A4, C5, D3; A4, C5, D4; A4, C5, D5; A4, C5, D6; A4, C5, D7; A4, C5, D8; A4, C5, D9;
A4, C6, D1; A4, C6, D2; A4, C6, D3; A4, C6, D4; A4, C6, D5; A4, C6, D6; A4, C6, D7; A4, C6, D8; A4, C6, D9;
A4, C7, D1; A4, C7, D2; A4, C7, D3; A4, C7, D4; A4, C7, D5; A4, C7, D6; A4, C7, D7; A4, C7, D8; A4, C7, D9;
A4, C8, D1; A4, C8, D2; A4, C8, D3; A4, C8, D4; A4, C8, D5; A4, C8, D6; A4, C8, D7; A4, C8, D8; A4, C8, D9;
A4, C9, D1; A4, C9, D2; A4, C9, D3; A4, C9, D4; A4, C9, D5; A4, C9, D6; A4, C9, D7; A4, C9, D8; A4, C9, D9;
A5, C1, D1; A5, C1, D2; A5, C1, D3; A5, C1, D4; A5, C1, D5; A5, C1, D6; A5, C1, D7; A5, C1, D8; A5, C1, D9;
A5, C2, D1; A5, C2, D2; A5, C2, D3; A5, C2, D4; A5, C2, D5; A5, C2, D6; A5, C2, D7; A5, C2, D8; A5, C2, D9;
A5, C3, D1; A5, C3, D2; A5, C3, D3; A5, C3, D4; A5, C3, D5; A5, C3, D6; A5, C3, D7; A5, C3, D8; A5, C3, D9;
A5, C4, D1; A5, C4, D2; A5, C4, D3; A5, C4, D4; A5, C4, D5; A5, C4, D6; A5, C4, D7; A5, C4, D8; A5, C4, D9;
A5, C5, D1; A5, C5, D2; A5, C5, D3; A5, C5, D4; A5, C5, D5; A5, C5, D6; A5, C5, D7; A5, C5, D8; A5, C5, D9;
A5, C6, D1; A5, C6, D2; A5, C6, D3; A5, C6, D4; A5, C6, D5; A5, C6, D6; A5, C6, D7; A5, C6, D8; A5, C6, D9;
A5, C7, D1; A5, C7, D2; A5, C7, D3; A5, C7, D4; A5, C7, D5; A5, C7, D6; A5, C7, D7; A5, C7, D8; A5, C7, D9;
A5, C8, D1; A5, C8, D2; A5, C8, D3; A5, C8, D4; A5, C8, D5; A5, C8, D6; A5, C8, D7; A5, C8, D8; A5, C8, D9;
A5, C9, D1; A5, C9, D2; A5, C9, D3; A5, C9, D4; A5, C9, D5; A5, C9, D6; A5, C9, D7; A5, C9, D8; A5, C9, D9;
A6, C1, D1; A6, C1, D2; A6, C1, D3; A6, C1, D4; A6, C1, D5; A6, C1, D6; A6, C1, D7; A6, C1, D8; A6, C1, D9;
A6, C2, D1; A6, C2, D2; A6, C2, D3; A6, C2, D4; A6, C2, D5; A6, C2, D6; A6, C2, D7; A6, C2, D8; A6, C2, D9;
A6, C3, D1; A6, C3, D2; A6, C3, D3; A6, C3, D4; A6, C3, D5; A6, C3, D6; A6, C3, D7; A6, C3, D8; A6, C3, D9;
A6, C4, D1; A6, C4, D2; A6, C4, D3; A6, C4, D4; A6, C4, D5; A6, C4, D6; A6, C4, D7; A6, C4, D8; A6, C4, D9;
A6, C5, D1; A6, C5, D2; A6, C5, D3; A6, C5, D4; A6, C5, D5; A6, C5, D6; A6, C5, D7; A6, C5, D8; A6, C5, D9;
A6, C6, D1; A6, C6, D2; A6, C6, D3; A6, C6, D4; A6, C6, D5; A6, C6, D6; A6, C6, D7; A6, C6, D8; A6, C6, D9;
A6, C7, D1; A6, C7, D2; A6, C7, D3; A6, C7, D4; A6, C7, D5; A6, C7, D6; A6, C7, D7; A6, C7, D8; A6, C7, D9;
A6, C8, D1; A6, C8, D2; A6, C8, D3; A6, C8, D4; A6, C8, D5; A6, C8, D6; A6, C8, D7; A6, C8, D8; A6, C8, D9;
A6, C9, D1; A6, C9, D2; A6, C9, D3; A6, C9, D4; A6, C9, D5; A6, C9, D6; A6, C9, D7; A6, C9, D8; A6, C9, D9;
A1, C1, E1; A1, C1, E2; A1, C1, E3;
A1, C2, E1; A1, C2, E2; A1, C2, E3;
A1, C3, E1; A1, C3, E2; A1, C3, E3;
A1, C4, E1; A1, C4, E2; A1, C4, E3;
A1, C5, E1; A1, C5, E2; A1, C5, E3;

A1, C6, E1; A1, C6, E2; A1, C6, E3;
A1, C7, E1; A1, C7, E2; A1, C7, E3;
A1, C8, E1; A1, C8, E2; A1, C8, E3;
A1, C9, E1; A1, C9, E2; A1, C9, E3;
A2, C1, E1; A2, C1, E2; A2, C1, E3;
A2, C2, E1; A2, C2, E2; A2, C2, E3;
A2, C3, E1; A2, C3, E2; A2, C3, E3;
A2, C4, E1; A2, C4, E2; A2, C4, E3;
A2, C5, E1; A2, C5, E2; A2, C5, E3;
A2, C6, E1; A2, C6, E2; A2, C6, E3;
A2, C7, E1; A2, C7, E2; A2, C7, E3;
A2, C8, E1; A2, C8, E2; A2, C8, E3;
A2, C9, E1; A2, C9, E2; A2, C9, E3;
A3, C1, E1; A3, C1, E2; A3, C1, E3;
A3, C2, E1; A3, C2, E2; A3, C2, E3;
A3, C3, E1; A3, C3, E2; A3, C3, E3;
A3, C4, E1; A3, C4, E2; A3, C4, E3;
A3, C5, E1; A3, C5, E2; A3, C5, E3;
A3, C6, E1; A3, C6, E2; A3, C6, E3;
A3, C7, E1; A3, C7, E2; A3, C7, E3;
A3, C8, E1; A3, C8, E2; A3, C8, E3;
A3, C9, E1; A3, C9, E2; A3, C9, E3;
A4, C1, E1; A4, C1, E2; A4, C1, E3;
A4, C2, E1; A4, C2, E2; A4, C2, E3;
A4, C3, E1; A4, C3, E2; A4, C3, E3;
A4, C4, E1; A4, C4, E2; A4, C4, E3;
A4, C5, E1; A4, C5, E2; A4, C5, E3;
A4, C6, E1; A4, C6, E2; A4, C6, E3;
A4, C7, E1; A4, C7, E2; A4, C7, E3;
A4, C8, E1; A4, C8, E2; A4, C8, E3;
A4, C9, E1; A4, C9, E2; A4, C9, E3;
A5, C1, E1; A5, C1, E2; A5, C1, E3;
A5, C2, E1; A5, C2, E2; A5, C2, E3;
A5, C3, E1; A5, C3, E2; A5, C3, E3;
A5, C4, E1; A5, C4, E2; A5, C4, E3;
A5, C5, E1; A5, C5, E2; A5, C5, E3;
A5, C6, E1; A5, C6, E2; A5, C6, E3;
A5, C7, E1; A5, C7, E2; A5, C7, E3;
A5, C8, E1; A5, C8, E2; A5, C8, E3;
A5, C9, E1; A5, C9, E2; A5, C9, E3;
A6, C1, E1; A6, C1, E2; A6, C1, E3;
A6, C2, E1; A6, C2, E2; A6, C2, E3;
A6, C3, E1; A6, C3, E2; A6, C3, E3;
A6, C4, E1; A6, C4, E2; A6, C4, E3;
A6, C5, E1; A6, C5, E2; A6, C5, E3;
A6, C6, E1; A6, C6, E2; A6, C6, E3;
A6, C7, E1; A6, C7, E2; A6, C7, E3;
A6, C8, E1; A6, C8, E2; A6, C8, E3;
A6, C9, E1; A6, C9, E2; A6, C9, E3;
A1, D1, E1; A1, D1, E2; A1, D1, E3;
A1, D2, E1; A1, D2, E2; A1, D2, E3;
A1, D3, E1; A1, D3, E2; A1, D3, E3;
A1, D4, E1; A1, D4, E2; A1, D4, E3;
A1, D5, E1; A1, D5, E2; A1, D5, E3;
A1, D6, E1; A1, D6, E2; A1, D6, E3;
A1, D7, E1; A1, D7, E2; A1, D7, E3;
A1, D8, E1; A1, D8, E2; A1, D8, E3;
A1, D9, E1; A1, D9, E2; A1, D9, E3;
A2, D1, E1; A2, D1, E2; A2, D1, E3;
A2, D2, E1; A2, D2, E2; A2, D2, E3;
A2, D3, E1; A2, D3, E2; A2, D3, E3;
A2, D4, E1; A2, D4, E2; A2, D4, E3;
A2, D5, E1; A2, D5, E2; A2, D5, E3;
A2, D6, E1; A2, D6, E2; A2, D6, E3;
A2, D7, E1; A2, D7, E2; A2, D7, E3;
A2, D8, E1; A2, D8, E2; A2, D8, E3;
A2, D9, E1; A2, D9, E2; A2, D9, E3;
A3, D1, E1; A3, D1, E2; A3, D1, E3;
A3, D2, E1; A3, D2, E2; A3, D2, E3;
A3, D3, E1; A3, D3, E2; A3, D3, E3;
A3, D4, E1; A3, D4, E2; A3, D4, E3;
A3, D5, E1; A3, D5, E2; A3, D5, E3;
A3, D6, E1; A3, D6, E2; A3, D6, E3;
A3, D7, E1; A3, D7, E2; A3, D7, E3;
A3, D8, E1; A3, D8, E2; A3, D8, E3;
A3, D9, E1; A3, D9, E2; A3, D9, E3;
A4, D1, E1; A4, D1, E2; A4, D1, E3;
A4, D2, E1; A4, D2, E2; A4, D2, E3;
A4, D3, E1; A4, D3, E2; A4, D3, E3;
A4, D4, E1; A4, D4, E2; A4, D4, E3;
A4, D5, E1; A4, D5, E2; A4, D5, E3;
A4, D6, E1; A4, D6, E2; A4, D6, E3;
A4, D7, E1; A4, D7, E2; A4, D7, E3;
A4, D8, E1; A4, D8, E2; A4, D8, E3;
A4, D9, E1; A4, D9, E2; A4, D9, E3;
A5, D1, E1; A5, D1, E2; A5, D1, E3;
A5, D2, E1; A5, D2, E2; A5, D2, E3;
A5, D3, E1; A5, D3, E2; A5, D3, E3;
A5, D4, E1; A5, D4, E2; A5, D4, E3;
A5, D5, E1; A5, D5, E2; A5, D5, E3;
A5, D6, E1; A5, D6, E2; A5, D6, E3;
A5, D7, E1; A5, D7, E2; A5, D7, E3;
A5, D8, E1; A5, D8, E2; A5, D8, E3;
A5, D9, E1; A5, D9, E2; A5, D9, E3;
A6, D1, E1; A6, D1, E2; A6, D1, E3;
A6, D2, E1; A6, D2, E2; A6, D2, E3;
A6, D3, E1; A6, D3, E2; A6, D3, E3;
A6, D4, E1; A6, D4, E2; A6, D4, E3;
A6, D5, E1; A6, D5, E2; A6, D5, E3;
A6, D6, E1; A6, D6, E2; A6, D6, E3;
A6, D7, E1; A6, D7, E2; A6, D7, E3;
A6, D8, E1; A6, D8, E2; A6, D8, E3;
A6, D9, E1; A6, D9, E2; A6, D9, E3;
B1, C1, D1; B1, C1, D2; B1, C1, D3; B1, C1, D4; B1, C1, D5; B1, C1, D6; B1, C1, D7; B1, C1, D8; B1, C1, D9;
B1, C2, D1; B1, C2, D2; B1, C2, D3; B1, C2, D4; B1, C2, D5; B1, C2, D6; B1, C2, D7; B1, C2, D8; B1, C2, D9;
B1, C3, D1; B1, C3, D2; B1, C3, D3; B1, C3, D4; B1, C3, D5; B1, C3, D6; B1, C3, D7; B1, C3, D8; B1, C3, D9;
B1, C4, D1; B1, C4, D2; B1, C4, D3; B1, C4, D4; B1, C4, D5; B1, C4, D6; B1, C4, D7; B1, C4, D8; B1, C4, D9;
B1, C5, D1; B1, C5, D2; B1, C5, D3; B1, C5, D4; B1, C5, D5; B1, C5, D6; B1, C5, D7; B1, C5, D8; B1, C5, D9;
B1, C6, D1; B1, C6, D2; B1, C6, D3; B1, C6, D4; B1, C6, D5; B1, C6, D6; B1, C6, D7; B1, C6, D8; B1, C6, D9;
B1, C7, D1; B1, C7, D2; B1, C7, D3; B1, C7, D4; B1, C7, D5; B1, C7, D6; B1, C7, D7; B1, C7, D8; B1, C7, D9;
B1, C8, D1; B1, C8, D2; B1, C8, D3; B1, C8, D4; B1, C8, D5; B1, C8, D6; B1, C8, D7; B1, C8, D8; B1, C8, D9;
B1, C9, D1; B1, C9, D2; B1, C9, D3; B1, C9, D4; B1, C9, D5; B1, C9, D6; B1, C9, D7; B1, C9, D8; B1, C9, D9;
B2, C1, D1; B2, C1, D2; B2, C1, D3; B2, C1, D4; B2, C1, D5; B2, C1, D6; B2, C1, D7; B2, C1, D8; B2, C1, D9;
B2, C2, D1; B2, C2, D2; B2, C2, D3; B2, C2, D4; B2, C2, D5; B2, C2, D6; B2, C2, D7; B2, C2, D8; B2, C2, D9;
B2, C3, D1; B2, C3, D2; B2, C3, D3; B2, C3, D4; B2, C3, D5; B2, C3, D6; B2, C3, D7; B2, C3, D8; B2, C3, D9;
B2, C4, D1; B2, C4, D2; B2, C4, D3; B2, C4, D4; B2, C4, D5; B2, C4, D6; B2, C4, D7; B2, C4, D8; B2, C4, D9;
B2, C5, D1; B2, C5, D2; B2, C5, D3; B2, C5, D4; B2, C5, D5; B2, C5, D6; B2, C5, D7; B2, C5, D8; B2, C5, D9;
B2, C6, D1; B2, C6, D2; B2, C6, D3; B2, C6, D4; B2, C6, D5; B2, C6, D6; B2, C6, D7; B2, C6, D8; B2, C6, D9;

B2, C7, D1; B2, C7, D2; B2, C7, D3; B2, C7, D4; B2, C7, D5; B2, C7, D6; B2, C7, D7; B2, C7, D8; B2, C7, D9;
B2, C8, D1; B2, C8, D2; B2, C8, D3; B2, C8, D4; B2, C8, D5; B2, C8, D6; B2, C8, D7; B2, C8, D8; B2, C8, D9;
B2, C9, D1; B2, C9, D2; B2, C9, D3; B2, C9, D4; B2, C9, D5; B2, C9, D6; B2, C9, D7; B2, C9, D8; B2, C9, D9;
B3, C1, D1; B3, C1, D2; B3, C1, D3; B3, C1, D4; B3, C1, D5; B3, C1, D6; B3, C1, D7; B3, C1, D8; B3, C1, D9;
B3, C2, D1; B3, C2, D2; B3, C2, D3; B3, C2, D4; B3, C2, D5; B3, C2, D6; B3, C2, D7; B3, C2, D8; B3, C2, D9;
B3, C3, D1; B3, C3, D2; B3, C3, D3; B3, C3, D4; B3, C3, D5; B3, C3, D6; B3, C3, D7; B3, C3, D8; B3, C3, D9;
B3, C4, D1; B3, C4, D2; B3, C4, D3; B3, C4, D4; B3, C4, D5; B3, C4, D6; B3, C4, D7; B3, C4, D8; B3, C4, D9;
B3, C5, D1; B3, C5, D2; B3, C5, D3; B3, C5, D4; B3, C5, D5; B3, C5, D6; B3, C5, D7; B3, C5, D8; B3, C5, D9;
B3, C6, D1; B3, C6, D2; B3, C6, D3; B3, C6, D4; B3, C6, D5; B3, C6, D6; B3, C6, D7; B3, C6, D8; B3, C6, D9;
B3, C7, D1; B3, C7, D2; B3, C7, D3; B3, C7, D4; B3, C7, D5; B3, C7, D6; B3, C7, D7; B3, C7, D8; B3, C7, D9;
B3, C8, D1; B3, C8, D2; B3, C8, D3; B3, C8, D4; B3, C8, D5; B3, C8, D6; B3, C8, D7; B3, C8, D8; B3, C8, D9;
B3, C9, D1; B3, C9, D2; B3, C9, D3; B3, C9, D4; B3, C9, D5; B3, C9, D6; B3, C9, D7; B3, C9, D8; B3, C9, D9;
B4, C1;D1; B4, C1, D2; B4, C1, D3; B4, C1, D4; B4, C1, D5; B4, C1, D6; B4, C1, D7; B4, C1, D8; B4, C1, D9;
B4, C2, D1; B4, C2, D2; B4, C2, D3; B4, C2, D4; B4, C2, D5; B4, C2, D6; B4, C2, D7; B4, C2, D8; B4, C2, D9;
B4, C3, D1; B4, C3, D2; B4, C3, D3; B4, C3, D4; B4, C3, D5; B4, C3, D6; B4, C3, D7; B4, C3, D8; B4, C3, D9;
B4, C4, D1; B4, C4, D2; B4, C4, D3; B4, C4, D4; B4, C4, D5; B4, C4, D6; B4, C4, D7; B4, C4, D8; B4, C4, D9;
B4, C5, D1; B4, C5, D2; B4, C5, D3; B4, C5, D4; B4, C5, D5; B4, C5, D6; B4, C5, D7; B4, C5, D8; B4, C5, D9;
B4, C6, D1; B4, C6, D2; B4, C6, D3; B4, C6, D4; B4, C6, D5; B4, C6, D6; B4, C6, D7; B4, C6, D8; B4, C6, D9;
B4, C7, D1; B4, C7, D2; B4, C7, D3; B4, C7, D4; B4, C7, D5; B4, C7, D6; B4, C7, D7; B4, C7, D8; B4, C7, D9;
B4, C8, D1; B4, C8, D2; B4, C8, D3; B4, C8, D4; B4, C8, D5; B4, C8, D6; B4, C8, D7; B4, C8, D8; B4, C8, D9;
B4, C9, D1; B4, C9, D2; B4, C9, D3; B4, C9, D4; B4, C9, D5; B4, C9, D6; B4, C9, D7; B4, C9, D8; B4, C9, D9;
B1, C1, E1; B1, C1, E2; B1, C1, E3;
B1, C2, E1; B1, C2, E2; B1, C2, E3;
B1, C3, E1; B1, C3, E2; B1, C3, E3;
B1, C4, E1; B1, C4, E2; B1, C4, E3;
B1, C5, E1; B1, C5, E2; B1, C5, E3;
B1, C6, E1; B1, C6, E2; B1, C6, E3;
B1, C7, E1; B1, C7, E2; B1, C7, E3;
B1, C8, E1; B1, C8, E2; B1, C8, E3;
B1, C9, E1; B1, C9, E2; B1, C9, E3;
B2, C1, E1; B2, C1, E2; B2, C1, E3;
B2, C2, E1; B2, C2, E2; B2, C2, E3;
B2, C3, E1; B2, C3, E2; B2, C3, E3;
B2, C4, E1; B2, C4, E2; B2, C4, E3;
B2, C5, E1; B2, C5, E2; B2, C5, E3;
B2, C6, E1; B2, C6, E2; B2, C6, E3;
B2, C7, E1; B2, C7, E2; B2, C7, E3;
B2, C8, E1; B2, C8, E2; B2, C8, E3;
B2, C9, E1; B2, C9, E2; B2, C9, E3;
B3, C1, E1; B3, C1, E2; B3, C1, E3;
B3, C2, E1; B3, C2, E2; B3, C2, E3;
B3, C3, E1; B3, C3, E2; B3, C3, E3;
B3, C4, E1; B3, C4, E2; B3, C4, E3;
B3, C5, E1; B3, C5, E2; B3, C5, E3;
B3, C6, E1; B3, C6, E2; B3, C6, E3;
B3, C7, E1; B3, C7, E2; B3, C7, E3;
B3, C8, E1; B3, C8, E2; B3, C8, E3;
B3, C9, E1; B3, C9, E2; B3, C9, E3;
B4, C1, E1; B4, C1, E2; B4, C1, E3;
B4, C2, E1; B4, C2, E2; B4, C2, E3;
B4, C3, E1; B4, C3, E2; B4, C3, E3;
B4, C4, E1; B4, C4, E2; B4, C4, E3;
B4, C5, E1; B4, C5, E2; B4, C5, E3;
B4, C6, E1; B4, C6, E2; B4, C6, E3;
B4, C7, E1; B4, C7, E2; B4, C7, E3;
B4, C8, E1; B4, C8, E2; B4, C8, E3;
B4, C9, E1; B4, C9, E2; B4, C9, E3;
B1, D1, E1; B1, D1, E2; B1, D1, E3;
B1, D2, E1; B1, D2, E2; B1, D2, E3;
B1, D3, E1; B1, D3, E2; B1, D3, E3;
B1, D4, E1; B1, D4, E2; B1, D4, E3;
B1, D5, E1; B1, D5, E2; B1, D5, E3;
B1, D6, E1; B1, D6, E2; B1, D6, E3;
B1, D7, E1; B1, D7, E2; B1, D7, E3;
B1, D8, E1; B1, D8, E2; B1, D8, E3;
B1, D9, E1; B1, D9, E2; B1, D9, E3;
B2, D1, E1; B2, D1, E2; B2, D1, E3;
B2, D2, E1; B2, D2, E2; B2, D2, E3;
B2, D3, E1; B2, D3, E2; B2, D3, E3;
B2, D4, E1; B2, D4, E2; B2, D4, E3;
B2, D5, E1; B2, D5, E2; B2, D5, E3;
B2, D6, E1; B2, D6, E2; B2, D6, E3;
B2, D7, E1; B2, D7, E2; B2, D7, E3;
B2, D8, E1; B2, D8, E2; B2, D8, E3;
B2, D9, E1; B2, D9, E2; B2, D9, E3;
B3, D1, E1; B3, D1, E2; B3, D1, E3;
B3, D2, E1; B3, D2, E2; B3, D2, E3;
B3, D3, E1; B3, D3, E2; B3, D3, E3;
B3, D4, E1; B3, D4, E2; B3, D4, E3;
B3, D5, E1; B3, D5, E2; B3, D5, E3;
B3, D6, E1; B3, D6, E2; B3, D6, E3;
B3, D7, E1; B3, D7, E2; B3, D7, E3;
B3, D8, E1; B3, D8, E2; B3, D8, E3;
B3, D9, E1; B3, D9, E2; B3, D9, E3;
B4, D1, E1; B4, D1, E2; B4, D1, E3;
B4, D2, E1; B4, D2, E2; B4, D2, E3;
B4, D3, E1; B4, D3, E2; B4, D3, E3;
B4, D4, E1; B4, D4, E2; B4, D4, E3;
B4, D5, E1; B4, D5, E2; B4, D5, E3;
B4, D6, E1; B4, D6, E2; B4, D6, E3;
B4, D7, E1; B4, D7, E2; B4, D7, E3;
B4, D8, E1; B4, D8, E2; B4, D8, E3;
B4, D9, E1; B4, D9, E2; B4, D9, E3;
C1, D1, E1; C1, D1, E2; C1, D1, E3;
C1, D2, E1; C1, D2, E2; C1, D2, E3;
C1, D3, E1; C1, D3, E2; C1, D3, E3;
C1, D4, E1; C1, D4, E2; C1, D4, E3;
C1, D5, E1; C1, D5, E2; C1, D5, E3;
C1, D6, E1; C1, D6, E2; C1, D6, E3;
C1, D7, E1; C1, D7, E2; C1, D7, E3;
C1, D8, E1; C1, D8, E2; C1, D8, E3;
C1, D9, E1; C1, D9, E2; C1, D9, E3;
C2, D1, E1; C2, D1, E2; C2, D1, E3;
C2, D2, E1; C2, D2, E2; C2, D2, E3;
C2, D3, E1; C2, D3, E2; C2, D3, E3;
C2, D4, E1; C2, D4, E2; C2, D4, E3;
C2, D5, E1; C2, D5, E2; C2, D5, E3;
C2, D6, E1; C2, D6, E2; C2, D6, E3;
C2, D7, E1; C2, D7, E2; C2, D7, E3;
C2, D8, E1; C2, D8, E2; C2, D8, E3;
C2, D9, E1; C2, D9, E2; C2, D9, E3;
C3, D1, E1; C3, D1, E2; C3, D1, E3;
C3, D2, E1; C3, D2, E2; C3, D2, E3;

C3, D3, E1; C3, D3, E2; C3, D3, E3;
C3, D4, E1; C3, D4, E2; C3, D4, E3;
C3, D5, E1; C3, D5, E2; C3, D5, E3;
C3, D6, E1; C3, D6, E2; C3, D6, E3;
C3, D7, E1; C3, D7, E2; C3, D7, E3;
C3, D8, E1; C3, D8, E2; C3, D8, E3;
C3, D9, E1; C3, D9, E2; C3, D9, E3;
C4, D1, E1; C4, D1, E2; C4, D1, E3;
C4, D2, E1; C4, D2, E2; C4, D2, E3;
C4, D3, E1; C4, D3, E2; C4, D3, E3;
C4, D4, E1; C4, D4, E2; C4, D4, E3;
C4, D5, E1; C4, D5, E2; C4, D5, E3;
C4, D6, E1; C4, D6, E2; C4, D6, E3;
C4, D7, E1; C4, D7, E2; C4, D7, E3;
C4, D8, E1; C4, D8, E2; C4, D8, E3;
C4, D9, E1; C4, D9, E2; C4, D9, E3;
C5, D1, E1; C5, D1, E2; C5, D1, E3;
C5, D2, E1; C5, D2, E2; C5, D2, E3;
C5, D3, E1; C5, D3, E2; C5, D3, E3;
C5, D4, E1; C5, D4, E2; C5, D4, E3;
C5, D5, E1; C5, D5, E2; C5, D5, E3;
C5, D6, E1; C5, D6, E2; C5, D6, E3;
C5, D7, E1; C5, D7, E2; C5, D7, E3;
C5, D8, E1; C5, D8, E2; C5, D8, E3;
C5, D9, E1; C5, D9, E2; C5, D9, E3;
C6, D1, E1; C6, D1, E2; C6, D1, E3;
C6, D2, E1; C6, D2, E2; C6, D2, E3;
C6, D3, E1; C6, D3, E2; C6, D3, E3;
C6, D4, E1; C6, D4, E2; C6, D4, E3;
C6, D5, E1; C6, D5, E2; C6, D5, E3;
C6, D6, E1; C6, D6, E2; C6, D6, E3;
C6, D7, E1; C6, D7, E2; C6, D7, E3;
C6, D8, E1; C6, D8, E2; C6, D8, E3;
C6, D9, E1; C6, D9, E2; C6, D9, E3;
C7, D1, E1; C7, D1, E2; C7, D1, E3;
C7, D2, E1; C7, D2, E2; C7, D2, E3;
C7, D3, E1; C7, D3, E2; C7, D3, E3;
C7, D4, E1; C7, D4, E2; C7, D4, E3;
C7, D5, E1; C7, D5, E2; C7, D5, E3;
C7, D6, E1; C7, D6, E2; C7, D6, E3;
C7, D7, E1; C7, D7, E2; C7, D7, E3;
C7, D8, E1; C7, D8, E2; C7, D8, E3;
C7, D9, E1; C7, D9, E2; C7, D9, E3;
C8, D1, E1; C8, D1, E2; C8, D1, E3;
C8, D2, E1; C8, D2, E2; C8, D2, E3;
C8, D3, E1; C8, D3, E2; C8, D3, E3;
C8, D4, E1; C8, D4, E2; C8, D4, E3;
C8, D5, E1; C8, D5, E2; C8, D5, E3;
C8, D6, E1; C8, D6, E2; C8, D6, E3;
C8, D7, E1; C8, D7, E2; C8, D7, E3;
C8, D8, E1; C8, D8, E2; C8, D8, E3;
C8, D9, E1; C8, D9, E2; C8, D9, E3;
C9, D1, E1; C9, D1, E2; C9, D1, E3;
C9, D2, E1; C9, D2, E2; C9, D2, E3;
C9, D3, E1; C9, D3, E2; C9, D3, E3;
C9, D4, E1; C9, D4, E2; C9, D4, E3;
C9, D5, E1; C9, D5, E2; C9, D5, E3;
C9, D6, E1; C9, D6, E2; C9, D6, E3;
C9, D7, E1; C9, D7, E2; C9, D7, E3;
C9, D8, E1; C9, D8, E2; C9, D8, E3;
C9, D9, E1; C9, D9, E2; C9, D9, E3;

Each of these combinations shows an overadditive effect in the treatment of inflammatory diseases especially respiratory diseases of inflammatory origin as asthma or COPD, or also rheumatism and auto-immune diseases.

Each of the combinations may be administered as fixed of free combinations, which may be administered simultaneously or one after the other.

Each of the combinations may be administered orally, topically, preferably inhalative. In free combinations the single active substances may be presented in the same or different administration forms, chosen from the possibilities of oral, topical, and inhalative application.

EXPERIMENTAL PART

The influence of monocompounds and their various combinations, also in three-in-one on TNF secretion was investigated by using human monocytes. The study was approved by our institutional Ethics Committee according to the International Declarations of Helsinki and Tokyo.

Peripheral blood mononuclear cells (PBMCs) were isolated from heparinized blood samples of healthy donors by density gradient centrifugation. An equal volume of Hanks buffer (Invitrogen, Heidelberg, Germany) was added to heparinized whole blood samples. 15 ml Histopaque-1077 (Sigma, Deisenhofen, Germany) were overlayed with a maximum of 40 ml of blood/Hanks mixture and were centrifuged for 30 min at room temperature (2000 rpm). A visible band containing PBMCs was transferred to a fresh tube and washed twice with Hanks-buffer. Finally cells are seeded in RPMI 1640 Medium (Life Technologies, Heidelberg, Germany) with Glutamax I (Gibco BRL, Eggenstein) and 10% FCS (Boehringer Mannheim, Penzberg, Germany). After isolated, PBMCs were seeded in RPMI 1640 medium (Invitrogen, Heidelberg, Germany) with Glutamax I (Invitrogen, Heidelberg, Germany). PBMCs were cultured in RPMI 1640 medium at 37° C. 5% $CO_2$ overnight. Monocytes were isolated from other cells by adherence method, non-adherent cells were removed by changing the medium.

Cells were re-suspended at $10^6$ cells/ml and incubated in 500 μl volumes in 24-well tissue culture plates (Falcon Becton Dickinson Labware, Heidelberg, Germany) at 37° C., 5% $CO_2$. After pre-incubation with test substances (0.5 μl/500 μl medium) for 30 min, cells were stimulated with lipopolysaccharide (LPS) (Sigma, Deisenhofen, Germany) (1 μg/ml). After 24 h of incubation, cells were sedimented by centrifugation. The supernatants were harvested and kept frozen at −80° C. until protein determination.

Cytokine measurements in culture supernatants were done by sandwich ELISA using matched antibody pairs (BD Pharmingen, Heidelberg, Germany). ELISA plates (Maxisorb, Nunc, Wiesbaden, Germany) were coated overnight with anti-cytokine monoclonal antibody (mAb) in 0.1M carbonate buffer, pH 9.5. After being washed, plates were blocked with Assay Diluent (BD Pharmingen, Heidelberg, Germany) for 1 h and washed again. Appropriately diluted supernatant samples and standards were distributed in duplicates and the plates were incubated for 2 h at room temperature. Plates were washed, incubated for 1 h with working detector (biotinylated anti-cytokine antibody and Avidin-horseradish peroxidase conjugate) (BD Pharmingen, Heidelberg, Germany). After washing, substrate (TMB and hydrogen peroxide) was added. The reaction was stopped by adding of 1M $H_3PO_4$. Plates were read at 450 nm (reference 570 nm) in a microplate reader (Dynatech, Alexandria, USA). The results were expressed as a percentage of the control level of cytokines production by cells stimulated in the absence of the compound.

Upon LPS-stimulation, basal TNFα release from monocytes increased from 328 pg/ml up to 7,258 pg/ml. R,R-glycopyrrolate alone did not influence the LPS-induced TNFα release up to 10 µmol/l.

The PDE4 inhibitor rolipram dose dependently inhibited the TNFα release. Maximum inhibition was around 70%. Consequently, instead of $IC_{50}$, the $IC_{35}$-value was determined. The $IC_{35}$ for rolipram amounted to 68.9±15.2 nM.

The corticosteroid budesonide also inhibited the TNFα release in a dose-dependent manner. The $IC_{50}$ for budesonide was 0.55±0.13 nM.

The $β_2$-adrenoceptor agonists formoterol in concentrations of up to 10 µM did not affect the LPS stimulated TNF-α release Based on the results from the single substances, in a first experiment the effect of the PDE4 inhibitor rolipram (10 nM) and the corticosteroid budesonide (0.1 nM) alone and in combination, and in combination with R,R-glycopyrrolate (10 µM) on the LPS-induced TNFα release from human PBMCs was investigated. The concentrations chosen for rolipram and budesonide were considerably below their $IC_{35}$ and $IC_{50}$, respectively. The results are summarized in FIG. 1.

The PDE4 inhibitor rolipram dose dependently inhibited the TNFα release. Maximum inhibition was around 70%. Consequently, instead of $IC_{50}$, the $IC_{35}$-value was determined. The $IC_{35}$ for rolipram amounted to 68.9±15.2 nM.

The corticosteroid budesonide also inhibited the TNFα release in a dose-dependent manner. The $IC_{50}$ for budesonide was 0.55±0.13 nM.

The $β_2$-adrenoceptor agonists formoterol in concentrations of up to 10 µM did not affect the LPS stimulated TNF-α release Based on the results from the single substances, in a first experiment the effect of the PDE4 inhibitor rolipram (10 nM) and the corticosteroid budesonide (0.1 nM) alone and in combination, and in combination with R,R-glycopyrrolate (10 µM) on the LPS-induced TNFα release from human PBMCs was investigated. The concentrations chosen for rolipram and budesonide were considerably below their $IC_{35}$ and $IC_{50}$, respectively. The results are summarized in FIG. 1.

Figure 1:
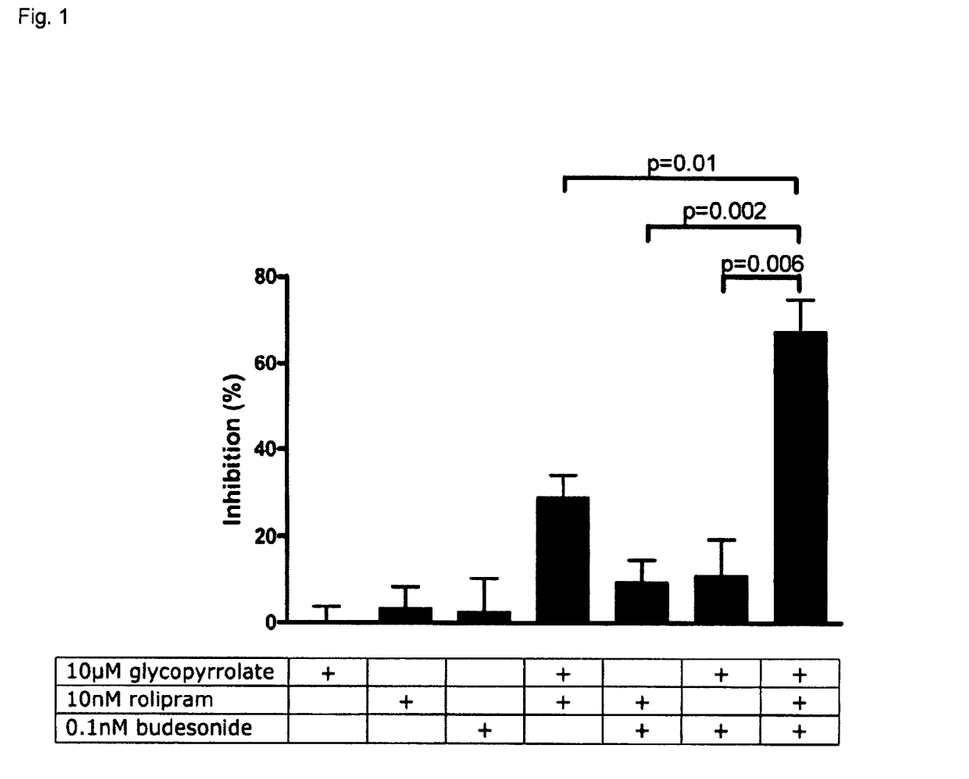
FIG. 1 shows the influence of glycopyrrolte, rolipram and budesonide and their combinations on the LPS stimulated TNF-α release from human monocytes. The y-axis indicates the inhibition of TNF-α release in %. The size of the columns shows the combination of substances and their amounts applied in the experiment. Statistically significant over-additive inhibition is indicated above the columns (p values).

As can be seen from FIG. 1, each drug alone hardly affected LPS-induced TNFα release. At the intentionally low concentrations, each double combination caused only a minor inhibition of TNFα secretion from PBMCs. In contrast, the three-in-one combination (budesonide, rolipram and R,R-glycopyrrolate) resulted in statistically significant over-additive inhibition of the TNFα release.

Figure 2:
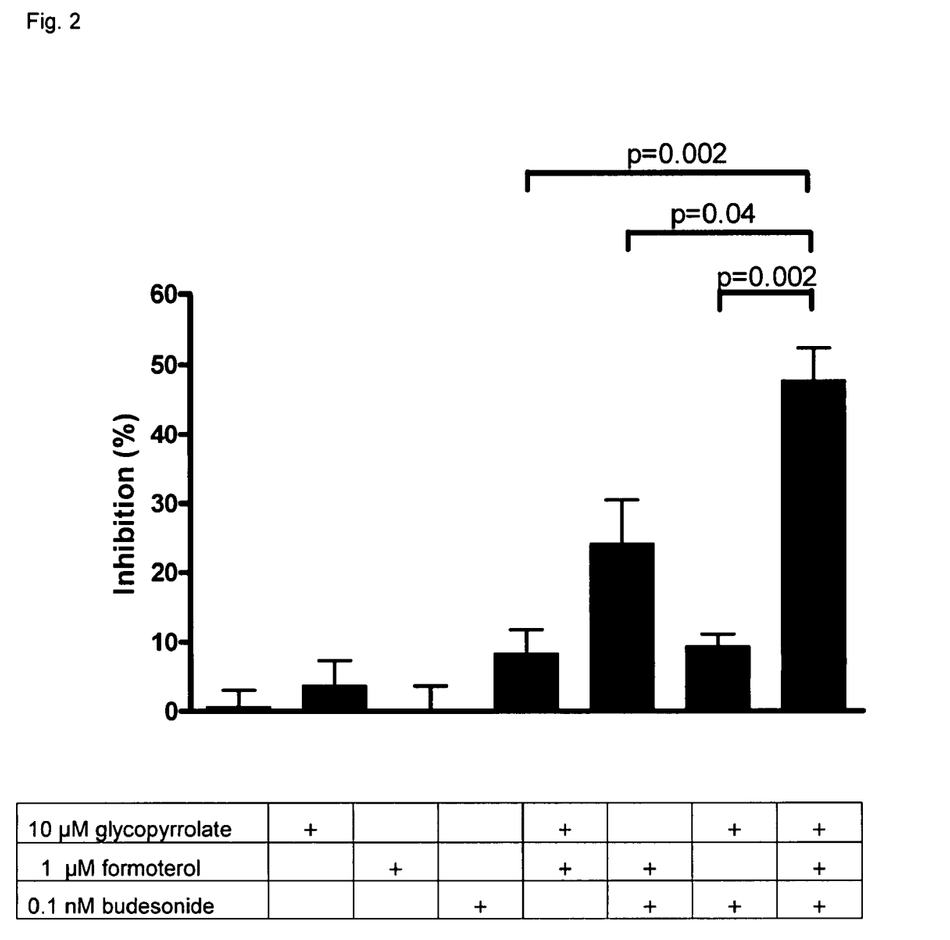
FIG. 2 shows the influence of glycopyrrolate, formoterol and budesonide and their combinations on the LPS stimulated TNF-α release from human monocytes. The y-axis indicates the inhibition of TNF-α release in %. The size of the columns shows the inhibition of TNF-α release for each combination of substances. The table below the columns shows the combination of substances and their amounts applied in the experiment. Statistically significant over-additive inhibition is indicated above the columns (p values).

Similar results were seen for the three-in-one combination (formoterol, budesonide and R,R-glycopyrrolate) which were evaluated in a second experiment. The double combination of R,R-glycopyrrolate/formoterol and R,R-glycopyrrolate/budesonide caused only a minor inhibition of TNF-α secretion. The double combination of formoterol/budesonide inhibited TNF-α secretion by about 25%. In contrast, the three-in-one combination of formoterol, budesonide and R,R-glycopyrrolate most effectively inhibited TNF-α secretion by about 50%. This over-additive effect was statistically significant. The results are summarized in FIG. 2.

The medications can be administered in different ways, such as metered-dosage inhalers (MDIs), in dry powder inhalers (DPIs), and in another liquid formulation suitable for inhalation. They can also be administered together in a single dosage form. Or they may be administered in different dosage forms. They may be administered at the same time. Or they may be administered either close in time or remotely, such as where one is administered in the morning and the second is administered in the evening. The combination may be used prophylactically or after the onset of symptoms has occurred. In some instances the combination(s) may be used to prevent the progression of a pulmonary disease or to arrest the decline of a function such as lung function.

These drugs, the anticholinergics, $β_2$-adrenoceptor agonist, the PDE4 inhibitors and GCs, are usually administered as an aerosol, or as an inhaled powder. Presently available LTRAs are administered orally. However, there is convincing evidence that LTRAs are also effective when they are given topically. Zafirlukast administered topically into the eyes effectively inhibit the development of symptoms and mediator release in an experimental model of allergic conjunctivitis in rats (Papathanassiou et al. Inflamm Res 2004; 53:373-6) indicating that they could also be administered as an aerosol or powder. This invention contemplates either co-administering all drugs in one delivery form such as an inhaler that is putting all drugs in the same inhaler.

As inhalable compositions pressurized metered dose inhalers, dry powders or inhalation solutions without propellant can be considered. Among the latter are even sterile, ready for use or just before use manufactured inhalation solutions, suspensions or concentrates as a nebulizable composition in an aqueous and/or organic medium. These dosage forms are part of the present invention.

Pressurized metered dose inhalers with propellants may contain the active substances in solution or in dispersion in a propellant. The propellants which can be used for inhalation aerosols in this invention are well known: mainly halogenated hydrocarbon derivatives, TG134a and TG227, or their mixtures are applied. Furthermore detergents (eg. oleic acid), stabilizers (eg. sodium edetate), co-solvents (eg. propyleneglycol, polyethyleneglycol, glycerol), antioxidants (eg. ascorbic acid), lubricants (eg. polyoxyethylene-glyceryl-trioleate) or buffer systems or other excipients for pH adjustment (eg. hydrochloric acid) are normally added. The active ingredient may have an average particle diameter of up to 5 µm.

A combination of ethyl alcohol and polyoxyethylene-25-glyceryl-trioleate (trade name: Tagat TO) can be suitable used as a detergent/stabilizer/co-solvent/lubricant complex in a concentration between 0.5 and 1.5%.

The above mentioned aerosols containing a propellant, solutions or suspensions according to the invention are administered by state of the art inhalers, so-called pressurized metered dose inhalers (=pMDI). They can be equipped with different-sized metal or plastic stems responsible for metering and release of the actives.

Administration of the medicament or pharmaceutical composition is preferably by inhalation. The inhalable form of the medicament may be, for example, an atomizable composition such as an aerosol comprising the active ingredients, separately or in admixture, in solution or dispersion in a propellant, or a nebulizable composition comprising a dispersion of the active ingredient in an aqueous/organic or medium. For example, the inhalable form of the medicament may be an aerosol comprising a mixture of any composition according to the invention in solution or dispersion in a propellant, or a combination of an aerosol containing each single active substance in solution or dispersion in a propellant. In another example, the inhalable form is a nebulized composition comprising a dispersion of the substances according to the inventive combination in an aqueous or organic medium, or a combination of dispersions of each substance in such a medium.

In another embodiment of the invention, the inhalable form is a dry powder, i.e. the substances are present in a dry powder comprising finely divided each substance optionally together with a finely divided pharmaceutically acceptable carrier, which is preferably present and may be chosen from materials known as carriers in dry powder inhalation compositions, for example saccharides, including monosaccharides, disaccharides, polysaccharides and sugar alcohols such as arabinose, fructose, ribose, mannose, sucrose, trehalose, lactose, starches, dextran or mannitol. An especially preferred carrier is lactose. The dry powder may be in capsules of gelatin or plastic, or in blisters, for in a dry powder inhalation device. Alternatively, the dry powder may be contained as a reservoir in a dose dry powder inhalation device.

The inhalation powders according to this invention can be administered by the help of state of the art dry powder inhalation devices for instance the Novolizer®. The inhalation powder can be pre-metered in capsules (eg. gelatine) or blisters (aluminium pouches) or metered just before use from a bulk reservoir. The active substances of the inventive combination can be there in a fixed combination or both actives are in separate packaging units, that they can be administered independent of each other from one device or a pack from two or more different devices or simultaneously.

In the finely divided particulate form of the medicament, and in the aerosol composition where the active ingredient is present in particulate form, the active ingredient may have an average particle diameter of up to 4 µm. The finely divided carrier, where present, generally has a maximum diameter up to approximately 500 µm and conveniently has a mean particle diameter of 10 to 350 µm, preferably approx. 110 to 290 µm. The particle size of the active ingredient, and that of the carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The active ingredients may be given from 1 to 8 times a day, sufficient to exhibit the desired activity. Preferably, the active components are given about once or four times a day, more preferably once or twice a day.

The inhaled anticholinergic drug, can be administered in an amount of between 5 and 500 µg/day adult human with the preference of 15 to 300 µg/day.

β2-adrenoceptor agonists can be administered in different amounts dependent on substance used, for example for formoterol nominal doses of 1 to 20 µg, for salmeterol 10 to 200 µg.

The PDE4 inhibitor can be administered in an amount between 10 and 5000 µg/day adult human with the preference of 50 to 2000 µg/day in dependence of the intensity of the airway inflammation.

The glucocorticoid can be administered in an amount of between 50 and 2000 µg/day adult human with the preference of 100 to 1000 mg/day in dependence of the intensity of the airway inflammation.

The LT-receptor antagonist can be administered in an amount of between 1 and 1000 µg/day adult human with the preference of 1 to 500 µg/day especially preferred 1 to 100 mg/day.

The active ingredients in all above aerosol formulations are preferably in the concentration of 0.01 wt % to 5 wt % of the total formulation.

For the treatment of Autoimmune diseases the drugs can preferably be administered either by oral route or rectally as enema.

The anticholinergic drug, R,R-glycopyrrolate can be administered in an amount between 1 and 199 mg/day for adult patients with the preference of 5 to 50 mg/day.

Basically, the initial doses of oral corticosteroids (for example prednisolone) may vary from 5 mg to 60 mg per day depending on the specific disease entity being treated. In situations of less severity lower doses will generally suffice while in selected patients higher initial doses may be required. The recommended dosage of budesonide is 6-9 mg daily.

The usual dosage of PDE4 inhibitors are different: for example for cilomilast, it is at 30 mg/day or for roflumilast, it varies between 0.25-1 mg/day.

The dosages of LTRAs vary over a great band width: For example the usual daily dose of montelukast amounts to 10 mg. Similarly, the daily dose of zafirlukast is 20 mg twice daily. However, the dose of pranlukast is 225 mg twice daily.

It is contemplated that all active agents would be administered at the same time, or very close in time. Alternatively, one drug could be taken in the morning and others later in the day. Or in another scenario, one drug could be taken twice daily and the others once daily, either at the same time as one of the twice-a-day dosing occurred, or separately. Preferably all drugs would be taken together at the same time.

We claim:

1. A combination comprising R,R-glycopyrrolate, rolipram and budesonide, or physiologically acceptable salts thereof, for the treatment of inflammatory diseases, wherein dosage amounts are such that a synergistic therapeutic effect is achieved.

2. The combination according to claim 1 wherein the inflammatory disease is a respiratory disease, rheumatism or an auto-immune disease.

3. The combination according to claim 2 wherein the respiratory disease is asthma or COPD.

4. The combination according to claim 2 wherein the auto-immune disease is rheumatoid arthritis, glomerulonephritis, multiple sclerosis, Crohn's disease, ulcerative colitis, systemic lupus erythematosus or psoriasis.

5. A pharmaceutical comprising the combination of claim 1 in a pharmaceutically acceptable form.

6. The pharmaceutical according to claim 5, that is an inhalable aerosol with or without propellant.

7. The pharmaceutical according to claim 5, that is an inhalable dry powder.

8. The pharmaceutical according to claim 5, that is an inhalable suspension or solution.

9. The pharmaceutical according to claim 5, presented in an inhaler.

10. The pharmaceutical according to claim 6, wherein the active substances are presented in fixed or free combination for simultaneous, sequential or separate administration together with acceptable excipients, adjuncts, and additives in a pharmaceutical form suitable for inhalative application.

* * * * *